United States Patent [19]
Alakhov et al.

[11] Patent Number: 5,817,321
[45] Date of Patent: Oct. 6, 1998

[54] BIOLOGICAL AGENT COMPOSITIONS

[75] Inventors: Valery Yu. Alakhov, Ouebec, Canada; Alexander V. Kabanov, Omaha, Nebr.; Peter G. Sveshnikov; Eugenii S. Severin, both of Moscow, Russian Federation

[73] Assignee: Supratek Pharma, Inc., Montreal, Canada

[21] Appl. No.: 478,978

[22] Filed: Jun. 7, 1995

Related U.S. Application Data

[63] Continuation-in-part of Ser. No. 374,406, Jan. 17, 1995, abandoned, which is a continuation of Ser. No. 957,998, Oct. 8, 1992, abandoned.

[51] Int. Cl.[6] ........................................................ A61K 9/00
[52] U.S. Cl. ........................ 424/400; 424/422; 514/772.5; 514/772.6; 514/772.7
[58] Field of Search .................................. 424/422, 400; 514/772.5, 772.6, 772.7

[56] References Cited

U.S. PATENT DOCUMENTS 5,143,731  9/1992  Viegas et al. ............................ 424/486

*Primary Examiner*—Thurman K. Page
*Assistant Examiner*—D. Faulkner
*Attorney, Agent, or Firm*—Mathews, Collins, Shepherd & Gould, P.A.

[57] ABSTRACT

The present invention relates to 1) pharmaceutical compositions and methods for chemotherapeutic agents and 2) pharmaceutical compositions for biological agents, particularly those whose target cells or tissues are resistant to the biological agent. The invention is targeted to overcome the resistance to biological agents that are developed by neoplasms and microbial infections. The formulation contains a biological agent and a polyether block copolymer. The block copolymer comprises an A-type linear polymeric segment joined at one end to a B-type linear polymeric segment; wherein the A type polymeric segment is hydrophilic, has repeating units which contribute an average Hansch-Leo fragmental constant of about 0.4 or less, and has a molecular weight contribution between 30 to about 500. The B-type segment is of relatively hydrophobic character, has repeating units which contribute an average Hansch-Leo fragmental constant of about −0.4 or more and a molecular weight contribution of about 30 to about 500, and has repeating units for each polymeric segment that comprise an ether linkage. The compositions may comprise chemotherapeutic agents, cytotoxic drugs, microbial treating agents, and a second biological agent.

42 Claims, 8 Drawing Sheets

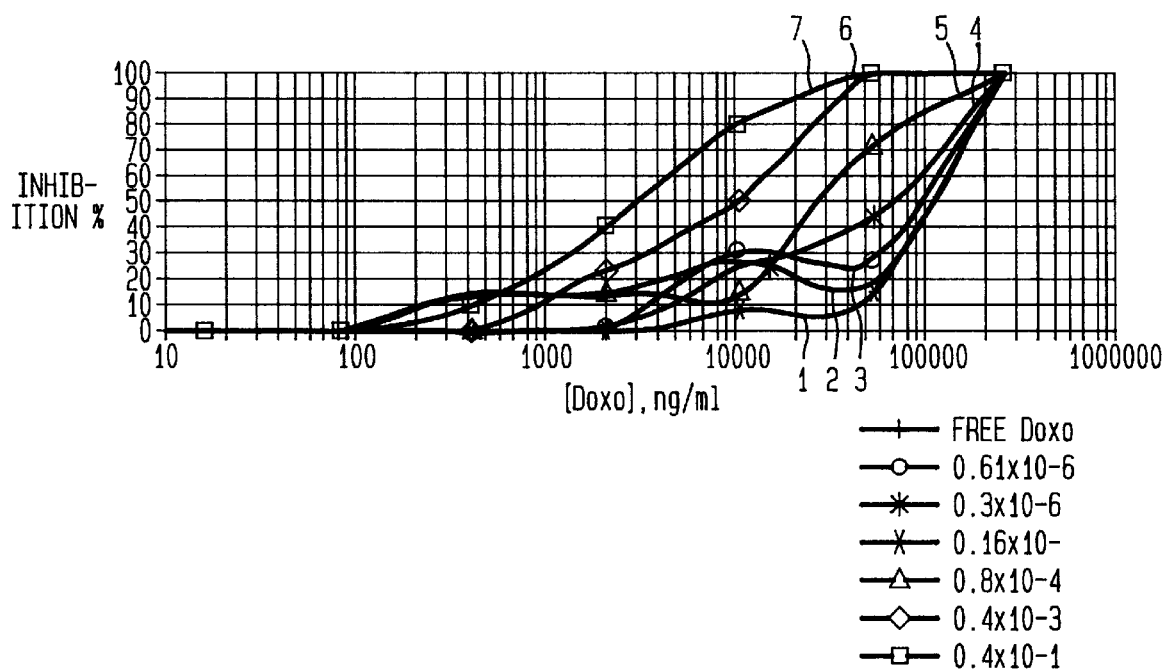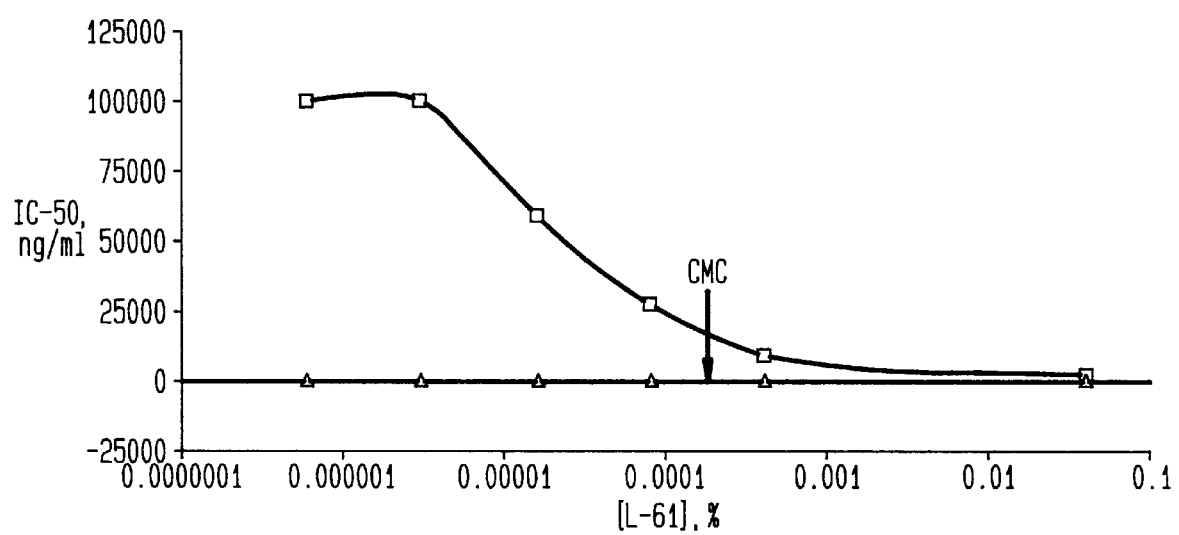

BIOLOGICAL AGENT COMPOSITIONS

This application is a continuation-in-part of U.S. application Ser. No. 08/374,406, filed Jan. 17, 1995, now abandoned, entitled "Improvements in Chemotherapeutic Compositions," which in turn is a continuation of U.S. Ser. No. 07/957,998, filed Oct. 8, 1992 now abandoned.

The present invention relates, among other things, to (1) pharmaceutical compositions and methods for chemotherapeutic agents and (2) pharmaceutical compositions for biological agents, particularly those whose target cells or tissues are resistant to the biological agent.

A number of chemotherapeutic agents exhibit low solubility and stability in physiological fluids. Often, chemotherapeutic agents are poorly transported across cell membranes. Further, many of these agents are binding with plasma proteins as well as other nonspecific interactions in the blood stream before they can reach the target cancer.

A major roadblock to effective chemotherapeutic treatments is the resistance to biological agents that many neoplasms and microbial infections develop. The sensitivity of neoplastic cells to anti-cancer agents can decrease by a factor as high as $10^3$ during the course of a chemotherapeutic regimen. When such resistance develops with respect to one agent, often the target cells are found to also be resistant to a number of other biological agents to which they had not previously been exposed. See Goldstein et al., *Crit. Rev. Oncol. Hematol.*, 12: 243–253, 1992; *Goodman and Gilman's The Pharmacological Basis of Therapeutics*, 8th Ed., McGraw-Hill, New York, 1994. One mechanism by which such resistance develops is believed to involve the membrane pump protein gp-170 (a glycoprotein P or P-gp protein). See Goldstein et al., *Crit. Rev. Oncol. Hematol.*, 12: 243–253, 1992.

It has now been discovered that these difficulties can be overcome by administering the biological agent in question in a formulation containing micelles of one or more block copolymers with the characteristics described below. Further, it has now been discovered that a certain subset of these block copolymers is particularly effective in delivering drugs and reversing resistance to a biological agent.

SUMMARY OF THE INVENTION

In one embodiment, the invention provides a pharmaceutical composition comprising:

(a) a biological agent; and (b) a polyether block copolymer comprising an A-type linear polymeric segment joined at one end to a B-type linear polymeric segment, wherein the A-type segment is of relatively hydrophilic character, the repeating units of which contribute an average Hansch-Leo fragmental constant of about –0.4 or less and have molecular weight contributions between about 30 and about 500, wherein the B-type segment is of relatively hydrophobic character, the repeating units of which contribute an average Hansch-Leo fragmental constant of about –0.4 or more and have molecular weight contributions between about 30 and about 500, wherein at least about 80% of the linkages joining the repeating units for each of the polymeric segments comprise an ether linkage. In a preferred first embodiment, the polyether block copolymer is selected from the group consisting of polymers of formulas $$A - B - A', \quad (I)$$
$$A - B, \quad (II)$$
$$B - A - B', \text{ or} \quad (III)$$
$$L(R^1)(R^2)(R^3)(R^4) \quad (IV)$$

wherein A and A' are A-type linear polymeric segments, B and B' are B-type linear polymeric segments, and $R^1$, $R^2$, $R^3$ and $R^4$ are either block copolymers of formulas (I), (II) or (III) or hydrogen and L is a linking group, with the proviso that no more than two of $R^1$, $R^2$ $R^3$ or $R^4$ are hydrogen.

In a preferred embodiment, the composition includes micelles of the block copolymer or forms micelles of the block copolymers during the course of administration or subsequent thereto. Preferably, at least about 0.1% of the biological agent is incorporated in the micelles, more preferably, at least about 1% of the biological agent, yet more preferably, at least about 5% of the biological agent.

In a preferred embodiment, the hydrophobe percentage of the copolymer of the composition is at least about 50% more preferably, at least about 60%, yet more preferably 70%.

In another preferred embodiment, the hydrophobe weight of the copolymer is at least about 900, more preferably, at least about 1700, yet more preferably at least about 2000, still more preferably at least about 2300.

In further preferred embodiments, the hydrophobe weight is at least about 2000 and the hydrophobe precentage is at least about 20%, preferably 35%; or the hydrophobe weight is at least about 2300 and the hydrophobe precentage is at least about 20%, preferably 35%.

In yet another preferred embodiment, the the copolymer or copolymers of the composition display a critical micellar concentration ("CMC") of no more than about 0.5% wt/vol at 37° C. in an isotonic aqeuous solution, preferably, no more than about 0.05% wt/vol, more preferably, no more than about 0.01% wt/vol, yet more preferably, no more than about 0.003% wt/vol.

Preferably, the copolymers of the composition conform to Formula (V), which is set forth in the text below. Particularly preferred among these copolymers are those having hydrophobe weights between about 1500 and about 2000, preferably between about 1710 and about 1780, and hydrophobe percentages between about 85% and about 95%, preferably between about 88% and about 92%. Also particularly preferred among these copolymers are those having hydrophobe weights between about 3000 and about 3500, preferably between about 3200 and about 3300, and hydrophobe percentages between about 15% and about 25%, preferably between about 18% and about 22%. Additionally particularly preferred among these polymers are that having hydrophobe weights between about 3500 and about 4000, preferably between about 3700 and about 3800, and hydrophobe percentages between about 25% and about 35%, preferably between about 28% and about 32%.

In a preferred embodiment, the composition comprises a chemotherapeutic agent.

In a second embodiment, the invention provides a pharmaceutical composition comprising a cytotoxic drug solubilized in polymeric micelles.

In another embodiment, the invention provides a method of treating a microbial infection or a tumor by administering a pharmaceutical composition of the first or second embodiment.

In yet another embodiment, the invention provides a method a treating a diseased tissue that has resistance to a biological agent during the course of a treatment with this or another biological agent, the method comprising administering a composition comprising (a) a second biological agent, which may be the same or different from the first biological agent, against which the tissue has resistance and (b) a micelle forming copolymer composition as described for the first or second embodiments of the invention.

In another embodiment, the invention provides a method of preventing or limiting tumor metastases by administering one of the anticancer compositions of the invention.

BRIEF DESCRIPTION OF THE DRAWINGS

FIGS. 3A and 3B show the inhibition of MCF7-ADR® cells incubated with various concentrations of doxorubicin and Pluronic L61.

DEFINITIONS

Figure 1:
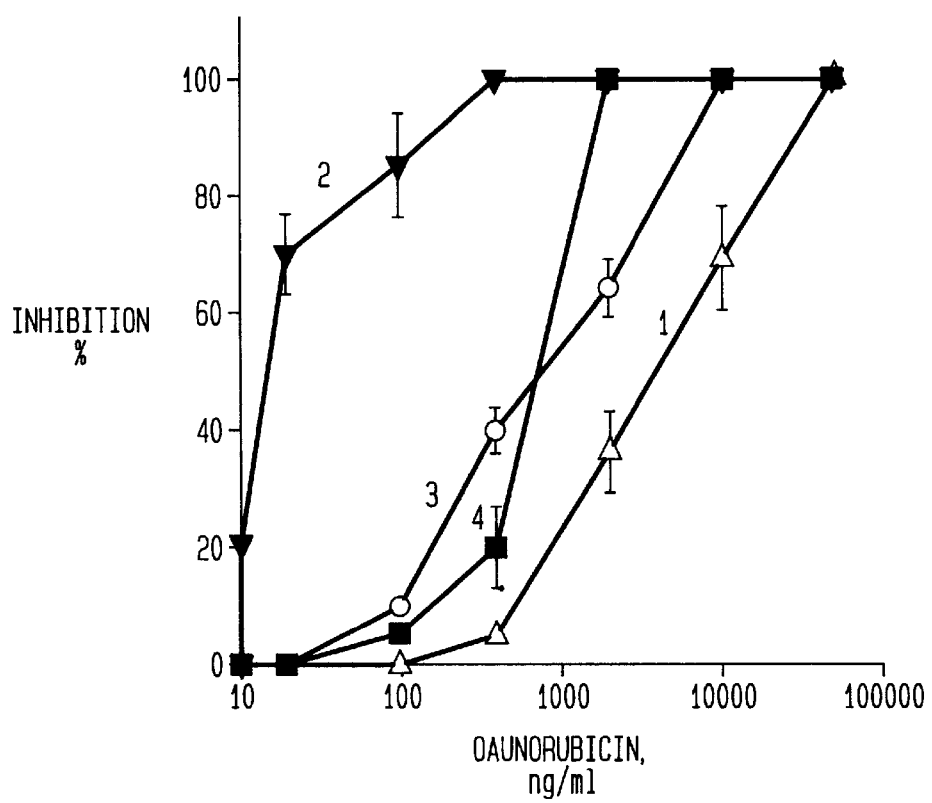
FIGS. 1 shows the cytotoxicity, for SK-resistant cells or SK cells treated with daunorubicin in free or micellar form.

The terms or phrases listed below shall have the following meaning:

| | |
|---|---|
| biological agent | an agent that is useful for diagnosing or imaging or that can act on a cell, organ or organism, including but not limited to drugs (pharmaceuticals) to create a change in the functioning of the cell, organ or organism. Such agents can include but are not limited to nucleic acids, polynucleotides, antibacterial agents, antiviral agents, antifungal agents, antiparasitic agents, tumoricidal or anti-cancer agents, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, anti-glaucomic agents, mydriatic compounds and local anesthetics. |
| chemotherapeutic agent | a biological agent that inhibits the growth or decreases the survival of neoplastic or pathogenic microbial cells or inhibits the propagation (which includes without limitation replication, viral assembly or cellular infection) of a virus. |
| cytotoxic drug | a chemotherapeutic agent useful in treating cancer that is cytotoxic, particularly to rapidly dividing cells. |
| hydrophobe percentage | the percentage of the molecular weight of a block copolymer that is made up of B-type blocks. This value is also referred to as the "hydrophobe weight percentage." |
| hydrophobe weight | the molecular weight contribution of the B-type blocks of a block copolyer. This value is also referred to as the "hydrophobe molecular weight." |
| IC$_{50}$ | the concentration at which 50% cytotoxicity is obtained. Cytotoxicity can be measured by the method of Alley et al., Cancer Res. 48: 589–601, 1988 or Scudiero et al., Cancer Res., 48:4827, 1988. In particular, it can be measured based on the drug concentration at which a 50% reduction in the activity of mitochondrial enzymes is observed. |
| lipophilic moiety | a lipophilic substituent that is joined to a targeting moiety and that partitions into the lipophilic portion of copolymer micelles to associate the targeting moiety with such micelles. |
| microbe | a bacteria, mycoplasma, yeast or fungi, virus or parasite (such as a malaria parasite). |
| MDR | cells are multidrug resistant (MDR) if they are resistent to the activity of biological agents that act on cell lines that are parental to the MDR cells. |
| targeting moiety | a molecular structure that is recognized by a cellular, tissue, viral or substratum component such as cell-surface receptor or acceptor molecule. |

DETAILED DESCRIPTION

It has been discovered that the effectiveness of the block copolymers of the invention in enhancing the potency of chemotherapeutic drugs and reversing MDR is highly dependent (a) on the hydrophobe percentage and (b) on the hydrophobe weight. The effectiveness increases with either an increase in the percentage (a) or an increase in weight (b), or both. These hydrophobe percentage and hydrophobe weight increases also correlate with improved micelle formation properties wherein micelle formation for these copolymers occurs at lower concentrations. See, Hurter et al., *Macromolecules* 26: 5030, 1993; Hurter et al., *Macromolecules* 26: 5592, 1993; Alexandris et al., *Macromolecules* 27: 2414, 1994. While not wishing to be limited to a particular theory, it is believed that micelle formation serves as a surrogate for measuring the physical properties that lead to improved biological agent delivery properties. Again, not wishing to be limited to a particular theory, it is believed that it is not micelles per se that lead to improved biological agent efficiency and reversion of multidrug resistance. If, using doxorubicin as a model biological agent, the ratio of (a) the IC$_{50}$ (a measure of effective cytotoxicity concentration) for a copolymer-containing composition to (b) the IC$_{50}$ for free doxorubicin is plotted against the concentration of copolymer, the plot is biphasic, with a rapid decrease in the ratio seen as copolymer concentrations increase but remain under the CMC of the copolymer. Above the CMC, a rapid leveling off of the ratio is observed. See FIG. 6B. Maximal enhancement of biological agent activity occurs above the CMC, although enhancement activity is seen at concentrations, for the copolymer Pluronic L61, as low as 0.0001% wt/vol, or less. The micellar form is also believed to be important to using the copolymers in drug delivery for other reasons, as will be discussed below.

The schematic below is helpful in understanding the relationship between the hydrophobe percentage and the hydrophobe weight of a copolymer and various aspects of the present invention. In the schematic, the weight of the hydrophobe (poly(oxypropylene)) and of the copolymer are shown directly under each identified copolymer. Adjacent to these values are the hydrophobe percentage values for each copolymer.

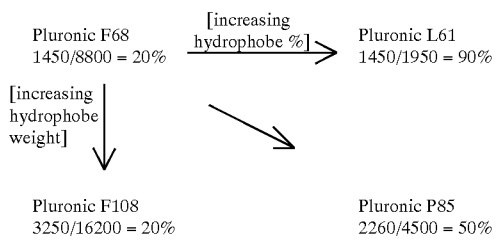

Pluronic F68 has been determined to have only a modest activity in enhancing the potency of biological agents. Pluronic L61, which has the same hydrophobe weight as Pluronic F68 but a much higher hydrophobe percentage, is generally the most effective of the block copolymers identified in the schematic. Pluronic F108, which has the same hydrophobe percentage as Pluronic F68 but a much higher hydrophobe weight, is also an effective copolymer, though much less effective than Pluronic L61. Pluronic P85 has a greater hydrophobe weight and a greater hydrophobe percentage than Pluronic F68, but the difference in each value is less than it is for Pluronics F108 and L61, respectively. The effectiveness of Pluronic P85 in enhancing the potency of biological agents is intermediate between the effectiveness of Pluronic F108 and of Pluronic L61. These differences in effectiveness are exemplified when various copolymers, at a concentration above CMC, and doxorubicin are incubated in vitro with drug-resistant cells. The ratio of the $IC_{50}$ value for cloxorubicin in the absence of copolymer to the ratio in the presence of copolymer is the "resistance reversion index." The resistance reversion index values for various copolymers are:

| Doxorubicin formulation | $IC_{50}$, ng/ml | Resistance reversion index |
|---|---|---|
| free drug | 60,000 | n.a. |
| +5% (w/v) Pluronic F68 | 60,000 | 1 |
| 0.01% (w/v) Pluronic F108 | 10,000 | 6 |
| 0.01% (w/v) Pluronic P85 | 2,000 | 30 |
| 0.01% (w/v) Pluronic L61 | 60 | 1000 |

The importance of the micellar form in delivering biological agents is also revealed in in vivo experiments. In the micellar form, biological agents are located in the hydrophobic core of the micelles, thereby masked by the hydrophilic shell (composed of A-type segments) surrounding the micelles. This masking decreases interactions with liver, plasma proteins, other non-target tissues and other molecules that can bind or inactivate the agent or convert the agent to a toxic metabolite. For example, rapid metabolism of anthracycline antibiotics by the liver leads to the formation of cardiotoxic metabolites that are modified at the C13 position. See, Mushlin et al., *Br. J. Pharmacol.* 110: 975–982, 1993. Using doxorubicin as a model drug, the micellar form decreases liver uptake, decreases conversion to doxorubicinol, and decreases the rate at which the concentration of doxorubicin in the blood decreases. See FIGS. 4 and 5.

The effectiveness of copolymers in (a) forming micelles (where greater effectiveness is measured in reduced CMCs) and (b) favoring the partitioning of various biological agents to the micellar rather than the free form increases according to the same pattern (i.e., with increases in hydrophobe weight or hydrophobe percentage). Thus, the hierarchy of effectiveness is again L61>P85>F108>>F68. The presence of micelles at low concentrations is believed to help assure, assuming that biological agent remains associated with the micelles, that the biological agent and the copolymer arrive together at a target tissue. Partitioning coefficients that favor the micellar form help assure that the assumption that the biological agent remains associated with micelles will hold true. The micellar form of the biological agent is also believed to protect the biological agent from uptake by non-target tissues, which tissues may metabolize the biological agent into an ineffective or toxic metabolite, and non-specific adsorption to blood components. cellular components and the like.

The same pattern of copolymer effectiveness applies in the treatment of experimental tumors with anti-cancer drugs, as illustrated in the examples.

At high concentrations, block copolymers can be toxic to the liver, kidney or other cells of a subject. See, BASF Corp., *Pluronic Material Safety Data Sheet and Drug Master Files*. The toxicity of block copolymers increases with the hydrophobicity parameters of block copolymers according to the same pattern seen for increases in effectiveness in potentiating biological agents. Fortunately, the rate of increase in potency as these hydrophobicity parameters change is much greater than the increase in copolymer toxicity. For instance, as illustrated in Example 8, the $LD_{50}$ of L61 in BALB/c mice is 10-fold lower than the $LD_{50}$ of Pluronic F108. However, the difference in the optimal therapeutic dose is more than 100-fold improved for Pluronic L61 vs. Pluronic F108 (see Example 9B). Thus, the concentration range over which effectiveness in potentiating the activity of a biological agent can be maintained while avoiding toxicity due to copolymer is increased for Pluronic L61 vs. Pluronic F108.

Members of the glycoprotein P family of membrane proteins are believed to be responsible for the multidrug resistance of many of the tumors whose resistance can be reversed using the compositions of the invention. See, Goldstein et al., *Cancer Treatment Res.* 57: 101–119, 1991. These proteins are believed to function as pumps that export the biological agent against which the tumors have become resistant. Members of the same protein family are believed to reside in the membranes of the endothelial cells lining blood vessels in the brain and to be responsible for the "blood-brain barrier" (BBB) that excludes effective amounts of many biological agents from the entering the brain. See, for example, Tatsuta et al., *J. Biol. Chem.* 267: 20383–20391. Compositions of the present invention can be used to enhance drug permeability into the brain, as discussed in more detail in U.S. application Ser. No. 08/478, 979, filed concurrently herewith on Jun. 7, 1995 and entitled "Compostions for Targeting Biological Agents," the entire disclosure of which is incorporated herein by reference. Further, members of this protein family are believed to be responsible for drug resistance in certain Candida, malaria and other microbial infections. Without wishing to be bound to a particular theory, it is believed that the compositions of the invention reverse efflux mechanisms mediated by members of the glycoprotein P family and other drug resistance mechanisms.

The invention is described with reference to the fragmental constants developed by Hansch and Leo. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. These constants were developed for use in estimating the contribution of a portion of a molecule to the tendency of the molecule to partition between the phases formed by octanol-water mixtures. These constants are generally referred to as Hansch-Leo fragmental partition constants (hereinafter "Hansch-Leo fragmental constants").

The compositions of the invention are generally intended to include either preformed micelles with a substantial portion of the biological agent dissolved therein, or copolymer compositions which form micelles with a substantial portion of the agent dissolved therein during the course of the administration of the biological agent to a patient or subsequent thereto. For the embodiments of the invention wherein targeting moieties are associated with the micelles, the targeting moiety will either be pre-associated with micelles or will associate with micelles during the course of administration. Particularly preferred block copolymers are those that have low CMC values in isotonic solutions at physiological temperatures. Such block copolymers will maintain a micellar delivery vehicle for biological agents even after substantial dilution into a physiological fluid such as a treatment subject's blood. Such low CMC values allow for the use of reduced levels of block copolymers in the drug composition of the invention.

The entire disclosure of U.S. application Ser. No. 08/374,406, filed Jan. 17, 1995, is incorporated herein by reference.

The number of repeating units of the total hydrophilic (A-type) blocks or the total hydrophobic (B-type) blocks of a polyether copolymer are preferably be between about 4 and about 400. More preferably, the number of repeating units is between about 4 and about 200, still more preferably, between about 5 and about 80. The repeating units that comprise the blocks, for A-type and B-type blocks, will generally have molecular weight between about 30 and about 500, preferably between about 30 and about 100, still more preferably between about 30 and about 60. Generally, in each of the A-type or B-type blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages (i.e., sugar linkages). However, in one aspect, simple ether linkages are preferred.

Preferably, all of the repeating units that comprise A-type blocks have a Hansch-Leo fragmental constant of less than about −0.4, more preferably, less than about −0.5, still more preferably, less than about −0.7. Preferably, all of the repeating units that comprise B-type blocks have a Hansch-Leo fragmental constant of about −0.30 or more, more preferably about −0.20 or more.

Polymers according to the first embodiment of the invention are exemplified by the block copolymers having the formulas:

$$HO\left[CH_2CH_2O\right]_x\left[\overset{CH_3}{\overset{|}{C}}HCH_2O\right]_y\left[CH_2CH_2O\right]_zH \qquad (V)$$

or, $$HO\left[CH_2CH_2O\right]_x\left[\overset{CH_3}{\overset{|}{C}}HCH_2O\right]_yH \qquad (VI)$$

or, $$HO\left[\overset{CH_3}{\overset{|}{C}}HCH_2O\right]_x\left[CH_2CH_2O\right]_y\left[\overset{CH_3}{\overset{|}{C}}HCH_2O\right]_zH \qquad (VII)$$

or,

-continued 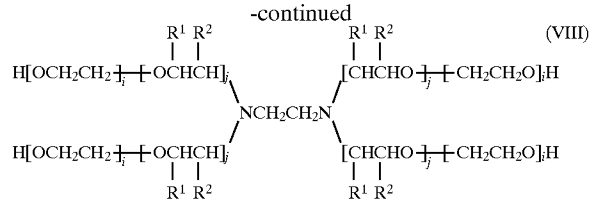 (VIII)

in which x, y, z, i and j have values consistent with the parameters for polyether copolymers described above, and wherein for each $R^1$, $R^2$ pair, one shall be hydrogen and the other shall be a methyl group. Formulas (V) through (VII) are oversimplified in that, in practice, the orientation of the isopropylene radicals within the B block will be random. This random orientation is indicated in formula (VIII), which is more complete. Such poly(oxyethylene)poly(oxypropylene) compounds have been described by Santon, *Am. Perfumer Cosmet.* 72(4): 54–58 (1958); *Schmolka, Loc. cit.* 82(7): 25–30 (1967); *Non-ionic Surfactants, Schick, ed.* (Dekker, New York, 1967), pp. 300–371. A number of such compounds are commercially available under such generic trade names as "poloxamers," "pluronics" and "synperonics." Pluronic polymers within the B-A-B formula are often referred to as "reversed" pluronics, "pluronic R" or "meroxapol." The "polyoxamine" polymer of formula (VIII) is available from BASF (Wyandotte, Mich.) under the tradename Tetronic™. The order of the polyoxyethylene and polyoxypropylene blocks represented in formula (VIII) can be reversed, creating Tetronic R™, also available from BASF. See, Schmolka, *J. Am. Oil Soc.,* 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

A number of pluronics are designed to meet the following formula:

$$HO\left[CH_2CH_2O\right]_{m/2}\left[\overset{CH_3}{\overset{|}{C}}HCH_2O\right]_n\left[CH_2CH_2O\right]_{m/2}H \qquad (IX)$$

Of course, the ordinarily skilled artisan will recognize that the values of m and n will usually represent a statistical average and that the number of repeating units of the first block of a given molecule will generally not be exactly the number of repeating units of the third block. The characteristics of a number of pluronics, described with reference to formula (IX), are as follows:

| Copolymer | Hydro-phobe weight | CMC (% w/v) | Hydrophobe percentage |
|---|---|---|---|
| Pluronic L61 | 1750 | 0.0003 | 90 |
| Pluronic L64 | 1750 | 0.002 | 60 |
| Pluronic F68 | 1750 | 4–5 | 20 |
| Pluronic P85 | 2250 | 0.005–0.007 | 50 |
| Pluronic F127 | 4000 | 0.003–0.005 | 30 |
| Pluronic F108 | 3250 | .003–0.007 | 20 |

These CMC values were determined by the surface tension method described in Kabanov et al., *Macromolecules* 28: 2303–2314, 1995.

Additional specific poly(oxyethylene)-poly(oxypropylene) block copolymers relevant to the invention include:

| Pluronic | Hydrophobe Weight | Hydrophobe Percentage |
|---|---|---|
| L31 | 950 | 90% |
| F35 | 950 | 50% |
| L42 | 1200 | 80% |
| L43 | 1200 | 70% |
| L44 | 1200 | 60% |
| L62 | 1750 | 80% |
| L63 | 1750 | 70% |
| L64 | 1750 | 60% |
| P65 | 1750 | 50% |
| L72 | 2050 | 80% |
| P75 | 2050 | 50% |
| L81 | 2250 | 90% |
| P84 | 2250 | 60% |
| F87 | 2250 | 30% |
| F88 | 2250 | 20% |
| L92 | 2750 | 80% |
| F98 | 2750 | 20% |
| L101 | 3250 | 90% |
| P103 | 3250 | 70% |
| P104 | 3250 | 60% |
| P105 | 3250 | 50% |
| F108 | 3250 | 20% |
| L121 | 4000 | 90% |
| L122 | 4000 | 80% |
| L123 | 4000 | 70% |
| F127 | 4000 | 30% |
| 10R5* | 1000 | 50% |
| 10R8 | 1000 | 20% |
| 12R3 | 1200 | 70% |
| 17R2 | 1700 | 80% |
| 17R1 | 1700 | 90% |
| 17R2 | 1700 | 80% |
| 17R4 | 1700 | 60% |
| 17R8 | 1700 | 20% |
| 22R4 | 2200 | 60% |
| 25R1 | 2500 | 90% |
| 25R2 | 2500 | 80% |
| 25R4 | 2500 | 60% |
| 25R5 | 2500 | 50% |
| 25R8 | 2500 | 50% |
| 31R1 | 3100 | 90% |
| 31R2 | 3100 | 80% |
| 31R4 | 3100 | 60% |

*All copolymers above this conform to formula (IX), this copolymer and those below conform to formula (VII).

The diamine-linked pluronic of formula (VIII) can also be a member of the family of diamine-linked polyoxyethylene-polyoxypropylene polymers of formula:

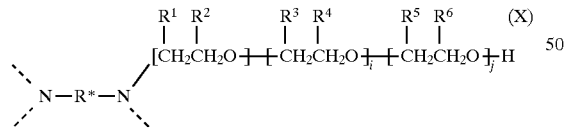

wherein the dashed lines represent symmetrical copies of the polyether extending off the second nitrogen, R* an alkylene of about 2 to about 6 carbons, a cycloalkylene of about 5 to about 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen. The —$NH_2$—$CH_2CH_2$—$NH_2$— group of of formula (VIII) and the N—R*—N group of formula (X) are examples of linking groups, L, of formula (IV).

Those of ordinary skill in the art will recognize, in light of the discussion herein, that even when the practice of the invention is confined for example, to poly(oxyethylene)-poly(oxypropylene) compounds, the above exemplary formulas are too confining. An important feature is that the average Hansch-Leo fragmental constant of the monomers in an A-type block be about −0.4 or less. Thus, the units making up the first block need not consist solely of ethylene oxide. Similarly, not all of the B-type block need consist solely of propylene oxide units. Instead, the blocks can incorporate monomers other than those defined in formulas (V)—(X), so long as the parameters of the first embodiment are maintained. Thus, in the simplest of examples, at least one of the monomers in block A might be substituted with a side chain group as previously described.

In another aspect, the invention relates to a drug composition made up of a block copolymer at least one of formulas (I)—(X), wherein the A-type and B-type blocks are substantially made up of repeating units of formula —O—$R^5$, where $R^5$ is:

(1) —$(CH_2)_n$—$CH(R^6)$—, wherein n is zero or an integer from about 1 to about 5 and $R^6$ is hydrogen, cycloalkyl having about 3 to about 8 carbon atoms, alkyl having about 1 to about 6 carbon atoms, phenyl, alkylphenyl wherein the alkyl has about 1 to about 6 carbon atoms, hydroxy, hydroxyalkyl, wherein the alkyl has about 1 to about 6 carbon atoms, alkoxy having about 1 to about 6 carbon atoms, an alkyl carbonyl having about 2 to about 7 carbon atoms, alkoxycarbonyl, wherein the alkoxy has about 1 to about 6 carbon atoms, alkoxycarbonylalkyl, wherein the alkoxy and alkyl each independently has about 1 about 6 carbon atoms, alkylcarboxyalkyl, wherein each alkyl independently has about 1 to about 6 carbon atoms, aminoalkyl wherein the alkyl has about 1 to about 6 carbon atoms, alkylamine or dialkylamino, wherein each alkyl independently has about 1 to about 6 carbon atoms, mono- or di-alkylaminoalkyl wherein each alkyl independently has about 1 to about 6 carbon atoms, chloro, chloroalkyl wherein the alkyl has from about 1 to about 6 carbon atoms, fluoro, fluoroalkyl wherein the alkyl has from about 1 to about 6 carbon atoms, cyano or cyano alkyl wherein the alkyl has from about 1 to about 6 carbon atoms or carboxyl;

(2) a carbocyclic group having about 3 to about 8 ring carbon atoms, wherein the group can be for example, cycloalkyl or aromatic groups, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substitutions, or (3) a heterocyclic group, having about 3 to about 8 ring atoms, which can include heterocycloalkyl or heteroaromatic groups, which can include from about 1 to about 4 heteroatoms selected from the group consisting of oxygen, nitrogen, sulfur and mixtures thereto, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 about 6 carbon atoms, amino, sulfonyl, hydroxy, carboxyl, fluoro or chloro substitutions.

Preferably, n is an integer from about 1 to about 3. The carbocyclic or heterocyclic groups comprising $R^5$ preferably have from about 4 to about 7 ring atoms, more preferably about 5 about 6. Heterocycles preferably include from about 1 to about 2 heteroatoms, more preferably, the heterocycles have one heteroatom. Preferably, the heterocycle is a carbohydrate or carbohydrate analog.

Those of ordinary skill will recognize that the monomers required to make these polymers are synthetically available. See, Vaughn et al., *J. Am. Oil Chem.* Soc. 28: 294, 1951. In some cases, polymerization of the monomers will require the use of suitable protective groups, as will be recognized by those of ordinary skill in the art. Generally, the A and B-type blocks are at least about 80% comprised of —$OR^5$— repeating units, more preferably at least about 90%, yet more preferably at least about 95%.

In another aspect, the invention relates to a drug composition made up of a block copolymer of one of formulas (I)—(X) wherein the A-type and B-type blocks consist essentially of repeating units of formula —O—$R^7$—, wherein $R^7$ is a $C_1$ to $C_6$ alkylene group.

The Hansch-Leo estimate of the octanol-water partitioning coefficient (P) for an organic molecule is calculated by the following formula:

$$\text{Log } P = \Sigma a_n f_n + \Sigma b_m F_m$$

where the $f_n$ values are the fragmental constants for the different groups in the molecule, the $a_n$ values are the number of any type of group in the molecule, the $F_m$ values are factors for certain molecular features such as single bonds or double bonds, and the $b_m$ values are the number of any such molecular feature. For instance, the Hansch-Leo fragmental constant for an ethylene oxide repeating unit (—$CH_2CH_2O$—) would be:

$$2f_C + 4f_H + f_O + (4-1)F_b = 2(0.20) + 4(0.23) + (-1.82) + 3(-0.12) = -0.86$$

The Hansch-Leo fragmental constant for a propylene oxide (—$CH_2CH(CH_3)O$—) repeating unit would be:

$$2f_C + f_{CH^3} + 3f_H + f_O + (4-1)F_b = 2(0.2) + 0.89 + 3(0.23) + (-1.82) + 3(-0.12) = -0.2$$

Those of ordinary skill in the art will recognize that the Hansch-Leo approach to estimating partition constants, in which approach the Hansch-Leo fragmental constants are applied, does not yield precisely the empirical partition constant. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. However, the approach is precise enough to define the hydrophobicity features of the polymeric delivery vehicle.

The block copolymers utilized in the invention will preferably form micelles in isotonic aqueous solutions at a physiological temperature having diameter from about 10 nm to about 100 nm. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a CMC that is characteristic of the amphiphile. By varying the sizes of the hydrophilic and hydrophobic segments of the block copolymers, the tendency of the copolymers to form micelles at physiological conditions, as well as the average size of the micelles formed at physiological conditions, can be varied. These tendencies can also be adjusted by blending copolymers with differing mixes of hydrophobic and hydrophilic blocks. The micelles have a dense core formed by the water insoluble repeating units of the B blocks and lipophilic portions of a biological agent dissolved therein, and a hydrophilic shell formed by the A blocks and hydrophobic portions of the biological agent. The micelles have translational and rotational freedom in aqueous environment, and aqueous environments containing the micelles have low viscosity similar to water. Micelle formation typically occurs at copolymer concentrations from about 0.0001 to 5% (w/v).

The small size of the micelles formed by block copolymers of the invention is believed to allow these micelles to penetrate in small capillaries and to be taken up by cells. The micelles also can incorporate large amounts of appropriate biological agents. For instance, micelles formed by Pluronic L61 can incorporate at least 1 mg of doxorubicin per 2 mg of copolymer.

The effective retention of a drug within the micelles of the invention can be quantified in terms of the partitioning coefficient (P) determined using formula:

$$P = [\text{Agent}]_m / [\text{Agent}]_{aq}$$

where $[\text{Agent}]_{aq}$ is the concentration of biological agent in an aqueous environment outside of the micelles and $[\text{Agent}]_m$ is the concentration of agent in the micelles. In some cases, P is facilely and accurately estimated based on the difference fluorescence properties of certain agents when in an aqueous vs. a more hydrophobic environment.

It will in some circumstances be desirable to incorporate, by noncovalent association, targeting molecules. See, for example, Kabanov et al., *J. Controlled Release,* 22:141 (1992) and U.S. application Ser. No. 08/478,979, filed concurrently herewith on Jun. 7, 1995 and entitled "Compositions for Targeting Biological Agents,". The targeting molecules that can be associated with the composition typically have a targeting moiety having affinity for a cellular site and a lipophilic moiety. The targeting molecules will spontaneously associate with the micelles and be "anchored" thereto through the lipophilic moiety. These targeting molecules will typically comprise about 10% or less of the copolymers in a composition.

In the targeting molecule, the lipophilic moiety can be, among other things, a lipid group such as a fatty acyl group. In a preferred embodiment, the lipophilic moiety is a hydrocarbon having from about 3 to about 41 carbon atoms, more preferably a hydrocarbon having from about 5 to about 25 carbon atoms, yet more preferably, a hydrocarbon having from about 9 to about 17 carbon atoms. Alternately, it can be a block copolymer or another natural synthetic polymer. The targeting group of the targeting molecule will frequently comprise an antibody, typically with specificity for a certain cell surface antigen. It could also be, for instance, a hormone having a specific interaction with a cell surface receptor, or a drug having a cell surface receptor. For example, glycolipids could serve to target a polysaccharide receptor. A non-limiting example of a targeting moiety is the anti-$\alpha_2$GP antibody to brain glial cells ($\alpha_2$-glycoprotein) which is described by Chekhonin et al., *FEBS Lett.* 287: 149–152, 1991.

For polyethylene oxide-polypropylene oxide copolymer, the hydrophilic/hydrophobic properties, and micelle forming properties of a block copolymer are related to the value of the ratio, n. The ratio, n, is defined as:

$$n=(|B|/|A|)\times(b/a)=(|B|/|A|)\times 1.32$$

where |B| and |A| are the number of repeating units in the hydrophobic and hydrophilic blocks of the copolymer, respectively, and b and a are the molecular weights for the respective repeating units. The value of n will typically be between about 0.2 and about 9.0, more preferably, between about 0.2 and about 1.5. Where mixtures of block copolymers are used, a value N will be used, which value will be the weighted average of n for each contributing copolymers, with the averaging based on the weight portions of the component copolymers. The value N can be used to estimate the micelle-forming properties of a mixture of copolymers. When copolymers other than polyethylene oxide-polypropylene oxide copolymers are used, similar approaches can be developed to relate the hydrophobic/hydrophilic properties of one member of the class of polymers to the properties of another member of the class.

In the second embodiment, the polymeric micelles are preferably formed of non-toxic, pharmaceutically acceptable polymers.

The pharmaceutical compositions of the invention can be administered by a number of routes, including without limitation orally, topically, rectally, vaginally, by pulmonary route, for instance, by use of an aerosol, or parenterally, including but not limited to intramuscularly, subcutaneously, intraperitoneally or intravenously. The compositions can be administered alone, or can be combined with a pharmaceutically-acceptable carrier or excipient according to standard pharmaceutical practice. For the oral mode of administration, the compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the compositions can be combined with emulsifying and suspending agents. If desired, certain sweetening and/or flavoring agents can be added. For parenteral administration, sterile solutions of the conjugate are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

Suppository forms of the compositions of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycola of various molecular weights and fatty acid esters of polyethylene glycol. See, Remington's Pharmaceutical *Sciences,* 16th Ed., Mack Publishing, Easton, Pa., 1980, pp. 1530–1533 for further discussion of suppository dosage forms. Analogous gels or creams can be used for vaginal, urethral and rectal administrations.

The chemotherapeutic agents appropriate for use in this invention include, without limitation, vinca alkaloids such as vincristine and vinblastine, mitomycin-type antibiotics such as mitomycin C and N-methyl mitomycin C, bleomycin-type antibiotics such as bleomycin $A_2$, antifolates such as methotrexate, aminopterin, and dideazatetrahydrofolic acid, colchicine, demecoline, etoposide, taxanes such as paclitaxel (Taxol$^R$), anthracycline antibiotics and others. The anthracycline antibiotics exemplify drugs having delivery problems due to low stability, the development of drug resistance in the target tissue, or rapid metabolism. These antibiotics typically include a fused tetracycline aglycone ring system joined at the 7-position to daunosamine. They include, for instance, the compounds represented by the formula:

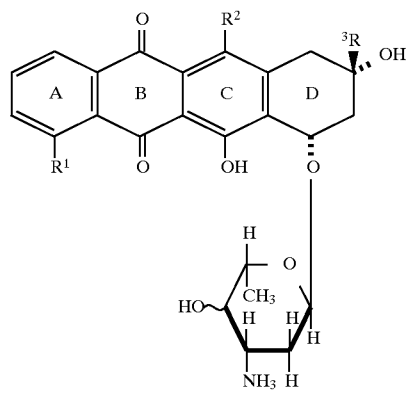

wherein $R^1$ is hydroxy or methoxy; $R^2$ is hydrogen or hydroxy; and $R^3$ is ethyl, acetyl, hydroxyacetyl, or an ester of hydroxyacetyl. These tetracycline antibiotics, like many anti-neoplastic agents, are believed to act by intercalating between the planar aromatic ring structures of DNA, thereby interfering with DNA replication. See, Neidle and Waring, *Molecular Aspects of Anti-Cancer Drug Action*, Pitman Press, 1983. Neoplastic cells are generally particularly susceptible, since they are actively replicating and thus synthesizing replica copies of their DNA. Such tetracycline antibiotics include, without limitation, doxorubicin daunorubicin, carminomycin, epirubicin, idarubicin, mithoxanthrone, 4-demethoxy-daunomycin, 11-deoxydaunorubicin, 13-deoxydaunorubicin, adriamycin-14-benzoate, adriamycin-14-octanoate or adriamycin-14-naphthaleneacetate.

Preferred classes of biological agents (including chemotherapeutic agents) include anti-neoplastic agents, antibacterial agents, antiparasitic agents, antifungal agents, CNS agents, immunomodulators and cytokines, toxins amd neuropeptides. Biological agents for which target cells tend to develop resistance mechanisms are also preferred. Particularly preferred biological agents include anthracyclines such as doxorubicin, daunorubicin, epirubicin, idarubicin, mithoxanthrone or carminomycin, vinca alkaloids, mitomycin-type antibiotics, bleomycin-type antibiotics, azole antifungals such as fluconazole, polyene antifungals such as amphotericin B, taxane-related antineoplastic agents such as paclitaxel and immunomodulators such as tumor necrosis factor alpha (TNFα), interferons and cytokines.

Preferred biological agents (including chemotherapeutic agents) include without limitation additional antifungal agents such as amphotericin B, flucytosine, ketoconazole, miconazole, itraconazole, griseofulvin, clotrimazole, econazole, terconazole, butoconazole, ciclopirox olamine, haloprogin, tolnaftate, naftifine, nystatin, natamycin, undecylenic acid, benzoic acid, salicylic acid, propionic acid and caprylic acid. Such agents further include without limitation antiviral agents such as zidovudine, acyclovir, ganciclovir, vidarabine, idoxuridine, trifluridine, foxcarnet, amantadine, rimantadine and ribavirin. Such agents further include without limitation antibacterial agents such as penicillin-related compounds including β-lactam antibiotics, broad spectrum penicillins and penicillinase-resistant penicillins (such as methicillin, nafcillin, oxacillin, cloxacillin, dicloxacillin, amoxicillin, ampicillin, ampicillin-sulbactam, azocillin, bacampicillin, carbenicillin, carbenicillin indanyl, cyclacillin, mezlocillin, penicillin G, penicillin V, piperacillin, ticarcillin, imipenem and aztreonam), cephalosporins (cephalosporins include first generation cephalosporins such as cephapirin, cefaxolin, cephalexin, cephradine and cefadroxil; second generation cephalosporins such as cefamandole, cefoxitin, cefaclor, cefuroxime, cefuroxime axetil, cefonicid, cefotetan and ceforanide; third generation cephalosporins such as cefotaxime, ceftizoxime, ceftriaxone, cefoperazone and ceftazidime), tetracyclines (such as demeclocytetracycline, doxycycline, methacycline, minocycline and oxytetracycline), beta-lactamase inhibitors (such as clavulanic acid), aminoglycosides (such as amikacin, gentamicin C, kanamycin A, neomycin B, netilmicin, streptomycin and tobramycin), chloramphenicol, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides (such as sulfanilamide, sulfamethoxazole, sulfacetamide, sulfadiazine, and sulfisoxazole), trimethoprim-sulfamethoxazole, quinolones (such as nalidixic acid, cinoxacin, norfloxacin and ciprofloxacin), methenamine, nitrofurantoin and phenazopyridine. Such agents further include agents active against protozoal infections such as chloroquine, diloxanide furoate, emetine or dehydroemetine, 8-hydroxyquinolines, metronidazole, quinacrine, melarsoprol, nifurtimox, pentamidine, sodium stibogluconate and suramin.

The dosage for a biological agent in a micellar composition will often be about that of the biological agent alone; dosages will be set by the prescribing medical professional considering many factors including the age, weight and condition of the patient and the pharmacokinetics of the agent. Often the amount of a micellar form of an agent required for effective treatment may be less than the amount required using the free biological agent. For daunorubicin use in treating cancer, a typical dosage will be about 1 mg per kg of body weight. Vinblastine is typically administered at a dose of from 0.1 to 0.2 mg per kg of body weight.

Generally, the biological agents used in the invention are administered to an animal in an effective amount. The effect of the copolymer used in the composition on effectiveness must be considered in determining effective amount. Generally, an effective amount is an amount effective to either (1) reduce the symptoms of the disease sought to be treated or (2) induce a pharmacological change relevant to treating the disease sought to be treated. For cancer, an effective amount includes an amount effective to: reduce the size of a tumor; slow the growth of a tumor; prevent or inhibit the formation of metastases; or increase the life expectancy of the affected animal.

In many cases, the metabolites of various biological agents create or enhance the unwanted effects resulting from administering the agent. This is certainly the case for anthracycline-based drugs, where metabolites are believed to lead to cardiotoxicity. See, Mushlin et al., *Br. J. Pharmacol.* 110: 975–982, 1993. The copolymer compositions of the invention can decrease the rate of metabolism for biological agents, thereby reducing the potential for harmful side effects.

Various antifungal agents successfully treat human fungal infections. However, the therapeutic dose is often a compromise between achieving effectiv drug levels and avoiding toxic side effects. In recent years, the emergence of drug resistance among intrinsically sensitive species such as Candida albicans and the increasing incidence of intrinsically drug resistant species such as Candida kruset has prompted a search for newer antifungal agents.

Although fluconazole has a low incidence of side effects, the incidence of resistance is an increasing problem. Delievery vehicles that are effective in enhancing chemotherapeutic activity and reversing resistance to such agents is therefore desireable for this agent, as well as for other antimicrobial agents.

The invention is exemplified by the following non-limiting examples.

EXAMPLE 1

Fatty acyl conjugates

A solution of 50 $\mu$l of 2 mg/ml of anti-$\alpha_2$GP antibody specific for the $\alpha_2$-glycoprotein of glial cells (Chekhomim et al., *FEBS Lett.* 287:149–152, 1991) in 0.1M borate buffer (pH 8.5) was mixed into 2 ml of 0.1M AOT® {sodium bis(2-ethylhexyl)sulfosuccinate, available from Serva Chemicals, Germany} in octane. A reaction is initiated by adding a two-fold molar excess (with respect to the polypeptide) of stearic acid chloride in 0.2ml of 0.1M AOT® in octane to the mixture. The stearic acid chloride was obtained from staric acid (available from Reakhim, Russia) as described in Kabanov et al., *Molek Biologiya* (Russian), 22: 473–484 (Engl. edn.: 382–391), 1988. The reaction was conducted overnight at 25° C. The product is precipitated three times with cold acetone, dissolved in RPMI 1640 medium and sterilely filtered through a 0.22 $\mu$m filter. (The polyclonal antibody used in this experiment also reacted with glial fibrillary acidic protein.)

EXAMPLE 2

Iodenated targeting moieties

Anti-$\alpha_2$GP antibody was labelled with $^{125}$I using Bolton-Hunter reagent in the system of reversed micelles of AOT® in octane as described in Slepnev V. I. et al., *Bioconjugate Chem.,* 3, 273–274 (1992). Specific radioactivity of the $^{125}$I-labelled protein ranges from 19 to 21 Ci/mol.

Wistar rats (80 g body weight, 8 animals/group) were injected i.p. (0.1 ml/10 g body weight) with a composition made up of the $^{125}$I-labelled anti-$\alpha_2$GP antibody (1 mCi/ml) dissolved in a mixture of 1.5% (w/v) copolymer Pluronic P85 and 2.5% (w/v) copolymer Pluronic L64 dissolved in RPMI 1640 medium. These copolymers, and all of the copolymers identified in the Examples, were obtained from Serva Chemicals, Germany. $^{125}$I-labelled polypeptide dissolved in RPMI 1640 medium was administered at the same concentration. After three days the animals were killed, and tissue samples taken for radioactivity assay to analyze tissue distribution as described by Chekhonin et al., *FEBS Lett.,* 287 149–152 (1991). The distribution of radioactivity was quantitated by liquid scintillation counting. The experiments were repeated at least twice and the results were reproducible with less than 10% variation. The results, expressed as the ratio of brain radioactivity to the radioactivity in a given tissue (±S.D.), were as follows:

| | Relative Content of Label | |
|---|---|---|
| Organ | Micelle | Control |
| Brain/heart | 1.22 ± 0.91 | 0.11 ± 0.02 |
| Brain/kidney | 7.42 ± 0.56 | 0.05 ± 0.01 |
| Brain/liver | 9.02 ± 0.75 | 0.01 ± 0.00 |
| Brain/lung | 12.1 ± 0.92 | 0.04 ± 0.01 |
| Brain/spleen | 6.48 ± 0.39 | 0.01 ± 0.00 |
| Brain/blood | 8.85 ± 0.67 | 0.01 ± 0.00 |

EXAMPLE 3A

Cytotoxicity against resistant cancer cells

Pluronic P85 was dissolved in RPMI 1640 medium (ICN Biomedicals Inc., Costa Mesa, Calif.) to a final concentration of 1%, and then the solution was sterilized by filtration to remove bacterial or fungal contamination. This Pluronic P85 solution was used to make appropriate dilutions of sterile drug solutions for the cell culture experiments described below.

The cytotoxicity studies utilized the SKOV3 line of transformed cells (hereinafter "SK cells") and the SKVLB cell line derived therefrom (hereinafter "SK-resistant cells"). Both of these cell lines were provided by Dr. V. Ling, University of Toronto. The SK-resistant cell line is a multi-drug resistant cell line derived from the SK cell line by long term cultivation in the presence of vinblastine.

Various dilutions of a number of anticancer agents were made in RPMI medium or the Pluronic P85 solution described above. Cells were prepared for use in these experiments by plating an equal volume of a cell suspension (2000–3000 cells) into the wells of 96-well microtiter plates (Costar, Cambridge, Mass.) and cultured for 2 days. All cell culturing was done at 37° C. and under a 5% $CO_2$ atmosphere. After this, 100 μl per plate of fresh medium (RPMI 1630 medium supplemented with 10% fetal calf serum) was added. The free anticancer agent or copolymer plus anticancer agent dilutions were applied to the wells in 100 μl volumes. The cells were exposed to the free or micellar form of a drug for two hours. After this incubation, the cells were washed three times with fresh medium. Then, the cells were cultured under fresh medium for an additional four days.

The number of viable cells for each culture was determined by standard XTT analysis, which measures the activity of mitochondrial enzymes. See, Scudiero et al., *Cancer Res.*, 48:4827 (1988). 50 μl per well of sterile 1 mg/ml XTT (2,3-bis[2Methoxy-4-nitro-5-sulfophenyl]-2H-tetrazolium-5-carboxanilide inner salt, Sigma, St. Louis, Mo.) in PRMI-1640 containing 5 μl/ml of 1.54 mg/ml phenazine metasulphate (Sigma) in PBS was added to the cells. The cells were incubated for 16 hours, after which the absorbance of each well at 450 nm was determined. The SEM for any value determined (the mean of three determinations) was always within 10% of the value. $IC_{50}$ values (i.e., the concentration at which 50% inhibition was achieved) were determined by extrapolating from graphs plotting the number of viable cells (i.e., the mitochondrial enzyme activity) versus the concentration of drug applied to the cells. The results for SK-resistant cells were as follows:

| Agent: | Daunorubicin | Vinblastine | Mitomycin C $IC_{50}$, (ng/ml) | Methotrexate | Cholchicine |
|---|---|---|---|---|---|
| Free agent | 6000 | 1200 | 2650 | 280 | 720 |
| Agent in 1% P85 | 16 | 1.1 | 5.0 | 17.5 | 45.0 |

The raw data that generated the daunorubicin data in the above chart is shown graphically in FIG. 1, where drug concentration is plotted against percent inhibition of mitochondrial activity in SK-resistant cells for the free drug (line 1) and the micellar form of the drug (line 2). The corresponding data for SK cells is shown in FIG. 1 for the free and micellar forms of the daunorubicin (lines 3 and 4, respectively).

EXAMPLE 3B

SK-resistance cells treated with various agents

The procedures described in Example 3A were used with SK-resistant cells. These cells were provided by Dr. V. Ling of the University of Toronto. The results were as follows:

| | $IC_{50}$, ng/ml | |
|---|---|---|
| Cytotoxic agent | Free agent | Agent + 1% P85 |
| Doxorubicin | 60,000 | 3,000 |
| Epirubicin | 60,000 | 2,000 |
| Vinblastine | 1,200 | 1.1 |
| Mitomycin C | 800 | 10 |
| Methotrexate | 500 | 90 |
| Colchicine | 720 | 45 |

EXAMPLE 3C

Kinetics of daunorubicin accumulation

Figure 2:
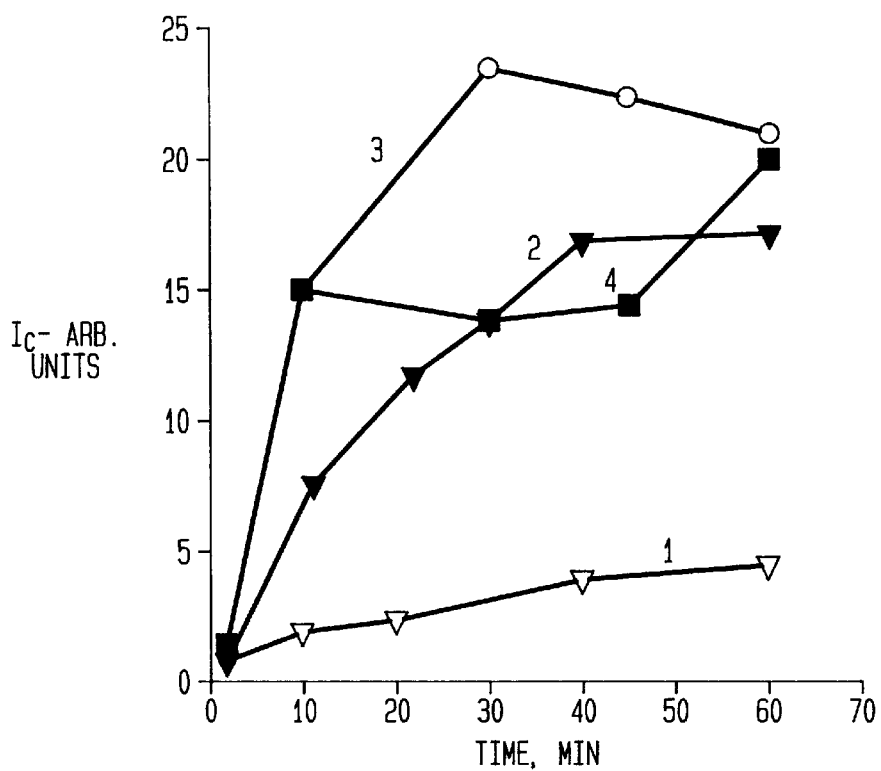
FIGS. 2 shows the kinetics of daunorubicin accumulation for SK-resistant cells or SK cells, respectively, treated with daunorubicin in free or micellar form.

The kinetics of daunorubicin accumulation in SK cells and SK-resistant cells was measured for cells treated with daunorubicin at 10 ng/ml by measuring the daunorubicin fluorescence accumulated in the cells ($\lambda_{ex}$=471 nm, $\lambda_{em}$=556 nm). The drug accumulation data for SK-resistant cells is displayed in FIG. 2 (line 1: free drug; line 2: micellar form); the data for SK cells is also displayed in FIG. 2 (line 3: free drug; line 4: micellar form).

EXAMPLE 3D

Doxorubicin titrations using different Pluronics

These experiments utilized the $CH^r$ C5 line of Chinese hamster ovarian carcinoma cells (provided by Dr. V. Ling or the Univ. of Toronto) and the methodology of Example 3A. For Pluronic L61 the concentration of copolymer applied to the cells was 0.01% (w/v); for Pluronic P85 the concentration was 0.01% (w/v); for Pluronic F108 the concentration was 0.01% (w/v); for Pluronic F68 the concentration was 5.0% (w/v). The $IC_{50}$ values were:

| Form of biological agent | $IC_{50}$, (ng/ml) |
|---|---|
| Free doxorubicin | 60,000 |
| Pluronic L61 | 70 |
| Pluronic P85 | 1000 |
| Pluronic F108 | 2000 |
| Pluronic F68 | 60,000 |

EXAMPLE 3E

Copolymer titrations

The methodology of Example 3A was used except in two details. The first difference was that doxorubicin-resistant MCF7 cells (MCF7-ADR® cells, which described further in Example 21) were used in place of SK cells. Second, in addition to varying doxorubicin concentrations, the concentration of copolymer was also varied. The percent inhibition with change in doxorubicin concentration is shown in FIG. 3A for cultures maintained in the presence of varying concentrations of Pluronic L61. Line 1 is for free doxorubicin; line 2 is for doxorubicin in the presence of $0.61 \times 10^{-6}$M Pluronic L61; line 3 is for doxorubicin in the presence of $0.3 \times 10^{-5}$M Pluronic L61; line 4 is for doxorubicin in the presence of $0.16 \times 10^{-4}$M Pluronic L61; line 5 is for doxorubicin in the presence of $0.8 \times 10^{-4}$M Pluronic L61; line 6 is for doxorubicin in the presence of $0.4 \times 10^{-3}$M Pluronic L61; and line 7 is for doxorubicin in the presence of $0.4 \times 10^{-1}$M Pluronic L61. In FIG. 3B, these data are consolidated such that the figure shows the $IC_{50}$ value for doxorubicin applied to the cells in the presence of the indicated concentration of Pluronic L61.

EXAMPLE 4
Copolymer cytotoxicity

Figure 3C:
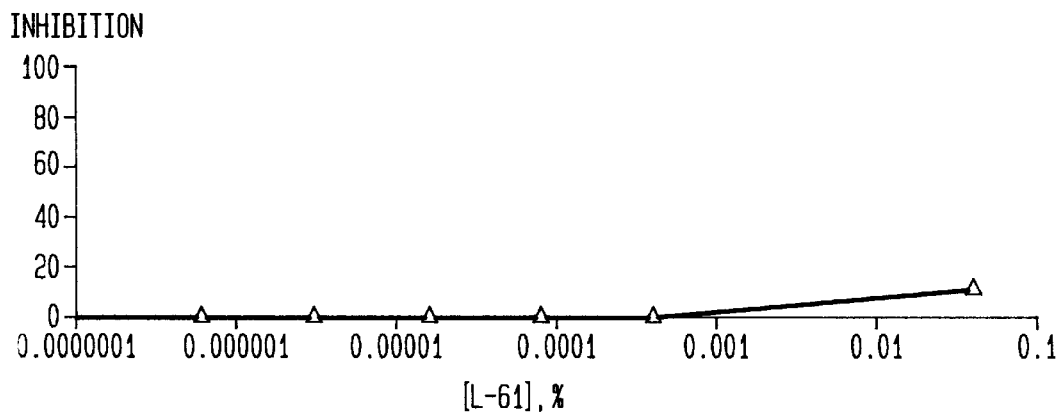
FIG. 3C shows the cellular toxicity of Pluronic L61 against MCF7-ADR® cells.

MCF7-ADR® cells (doxarubicin resistant cells described in Example 21) were incubated with Pluronic L61 at various concentrations and cytotoxicity was determined as described in Example 3A. The results are shown in FIG. 3C.

EXAMPLE 5A
Polymer biodistribution

Radioactive, tritium-containing derivatives of Pluronic P85 polymers were obtained from Kurchatov Institute of Atomic Energy, Moscow, Russia. 100 µl per 20 g of body weight of a 1% w/v isotonic solution of the radioactive copolymer ($2 \times 10^7$ cpm/20 g body weight) was administered iv. into (a) BALB/c mice (from Kriukovo Veterinary Dept. of Russian Acad. Medical Sciences, Moscow, Russia) and (b) BALB/c mice into which $3 \times 10^6$ SP2/0$^{dnr}$ murine myeloma cells (described in Example 9A) had been injected subcutaneously 6 weeks previously. The biodistribution of polymer at various times post-injection of the radioactive copolymer was measured by sacrificing treated mice at the various timepoints, excising the tissues listed in the tables below, and quantifying the distribution of radioactivity by liquid scintillation counting. To prepare tissue samples for liquid scintillation counting, samples were placed in 1 ml of tissue solubilizer (available from Serva Chemicals, Germany) and homogenized in the cold. The homogenates were incubated for hours at room temperature, decolorized with 50 µl of 30% hydrogen peroxide, and incubated overnight at room temperature.

For BALB/c mice lacking injected tumor cells, the results were:

| Organ | Polymer content (% of initial dose per organ) | | |
|---|---|---|---|
|  | 73 hours | 92.5 hours | 121 hours |
| Spleen | 0.23 | 0.2 | 0.12 |
| Liver | 3.69 | 3.27 | 1.8 |

For BALB/c mice with injected tumor cells, the results were:

| Organ | Polymer content (% of initial dose per organ) | | |
|---|---|---|---|
|  | 73 hours | 92.5 hours | 121 hours |
| Spleen | 0.35 | 0.47 | 0.36 |
| Liver | 3.71 | 3.35 | 3.35 |
| Tumor | 1.53 | 6.24 | 1.50 |

Additional observations derived from this set of experiments were (1) that degradation products of the polymers were not observed until 24 hours after polymer administration and (2) complete clearance of polymer from the mice occurred 250 to 300 hours after administration.

EXAMPLE 6A
Blood concentrations of copolymer

Figure 4:
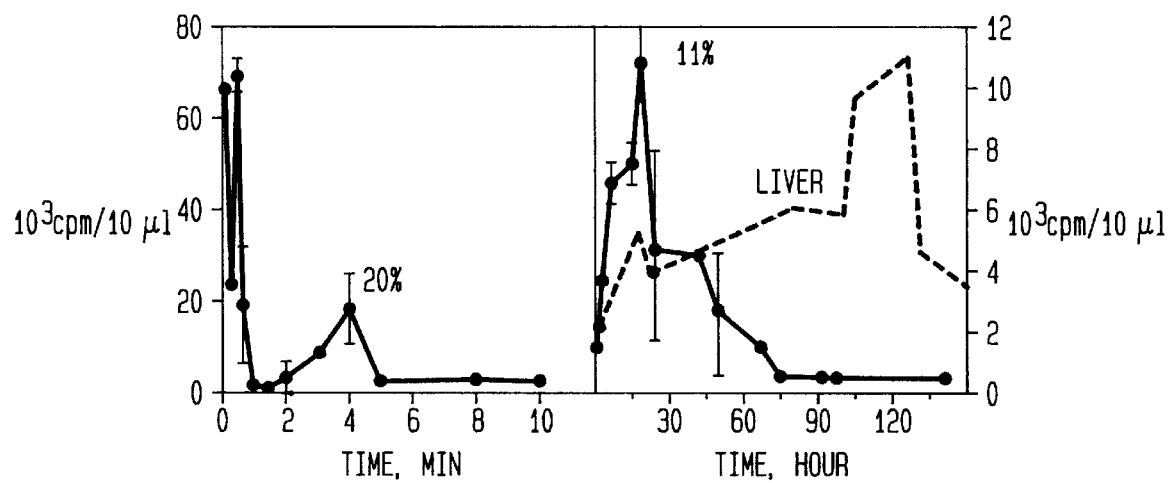
FIG. 4 shows the time course of clearance of [$^3$H]-Pluronic P85 from the blood and accumulation in the liver.

100 µl/20 g body weight of the [$^3$H]-Pluronic P85 of Example 4 were administered to 6-week old BALB/c mice by i.v. injection. FIG. 4 shows the amount of radioactivity found in the blood of the mice at various timepoints post-injection (dark line) and in the liver (dashed line).

EXAMPLE 6B
Blood concentrations of copolymer

Figure 5:
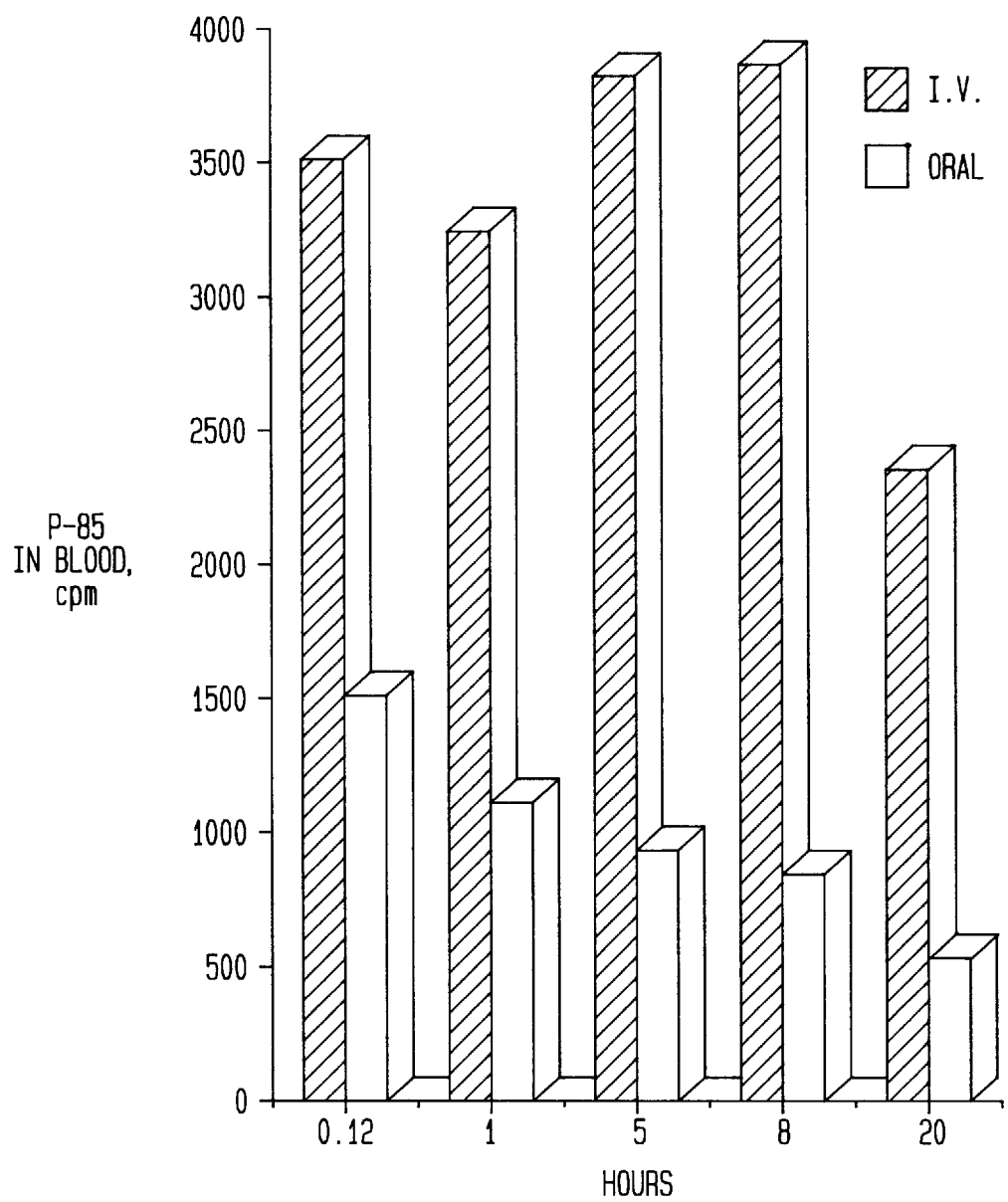
FIG. 5 shows a comparison of the blood concentration of [$^3$H]-Pluronic P85 administered i.v. or orally.

100 µl/20 g body weight of the [$^3$H]-Pluronic P85 of Example 4 were administered to 6-week old BALB/c mice by i.v. injection or orally. The amount of radioactivity found in the blood of the mice at various timepoints post injection is shown in FIG. 5, where the first bar in each pair is for i.v. injected polymer, and the second bar is for orally administered polymer.

EXAMPLE 7
Daunorubicin and daunorubicinol pharmacokinetics

Figure 6A:
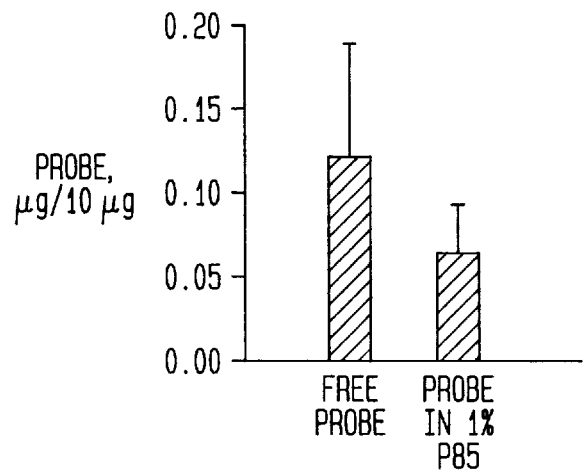
FIG. 6A shows liver concentrations of daunorubicin.
Figure 6B:
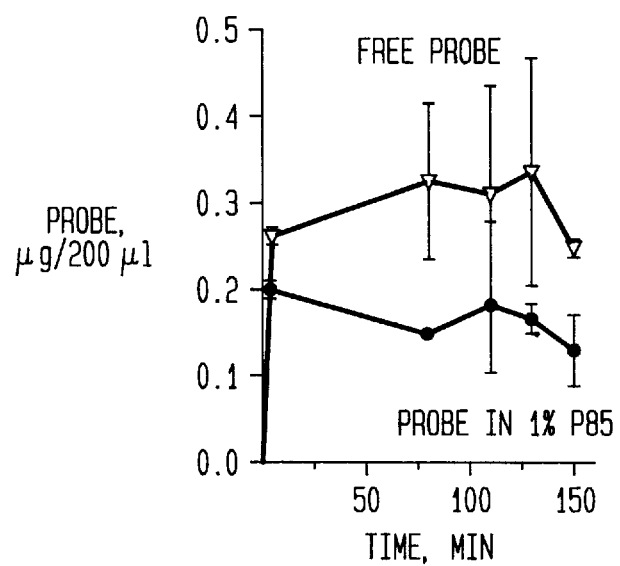
FIG. 6B shows blood concentrations of daunorubicinol over time post-injection.
Figure 6C:
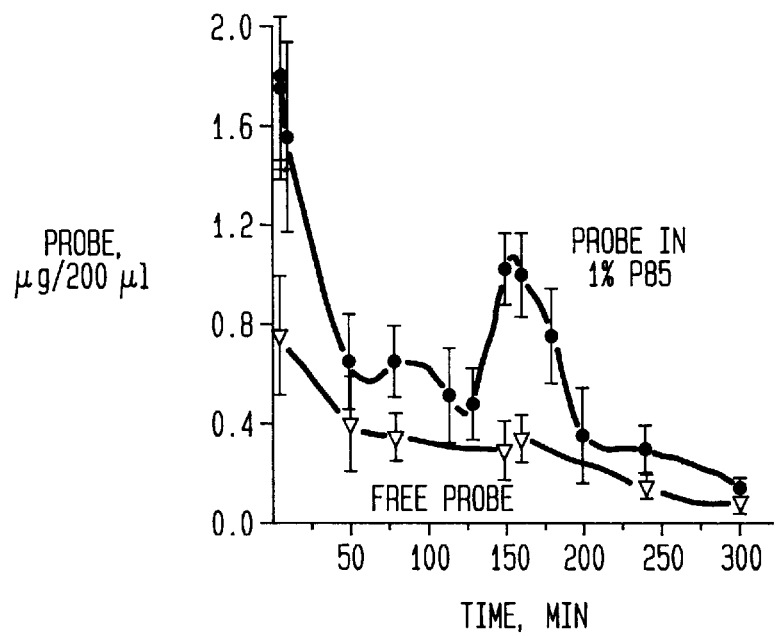
FIG. 6C shows blood concentrations of daunorubicin over time post-injection.

Daunorubicin metabolism was monitored by HPLC. Daunorubicin (Sigma, St. Louis, Mo.) was injected i.v. into 7-week-old C57B1/6 mice at 10 mg/kg body weight using a saline vehicle or a saline vehicle containing 1% w/v Pluronic P85. Injection volumes were 100 µl/20 g body weight. At various times after injection, the animals were sacrificed and blood and liver homogenate were extracted with chloroform: methanol 9:1. The extracts were dried and redissolved in aqueous 0.1% trifluoroacetic acid (TFA). The solubilized extract was injected onto a 4.6×150 mm C18, reversed-phase HPLC column (15 micron Ultrasphere, Beckman, Calif.). The column was developed with a 0 to 40 acetonitrile gradient in 0.1% TFA and the peaks for daunorubicin and its metabolite daunorubicinol were identified and quantified. FIG. 6A shows the concentration of daunorubicin in liver at 150 minutes post-injection, with bar A showing the level for free daunorubicin (µg per 10 µg of liver tissue) and bar B showing the level for the copolymer formulation. FIG. 6B shows the time course of daunorubicinol accumulation in the blood for mice administered free daunorubicin (line 1) or the copolymer form (line 2). FIG. 6C shows the time course of daunorubicin accumulation in the blood for mice administered free daunorubicin (line 1) or the copolymer form (line 2).

EXAMPLE 8
Acute toxicity

The acute toxicity of Pluronic F108, P85 and L61 were studies in 5-week old BALB/c male mice. Each experimental group of mice included 6 mice. Various doses of isotonic Pluronic solutions were administered i.p. Animal mortality was monitored daily for 14 days. The $LD_{50}$ and maximum tolerated dosage ("MTD", i.e., the maximal dose at which no animals among 6 equivalently treated animals died) were calculated by probit analysis. See, Chan and Hayes in *Principles and Methods of Toxicology*, Hayes, A. W., ed., Raven Press, New York, 1989, pp. 169–189. The results were as follows:

| Pluronic | MTD, g/kg | $LD_{50}$, g/kg |
|---|---|---|
| Pluronic LG1 | 0.1 | 0.8 |
| Pluronic P85 | 0.2 | 0.8 |
| Pluronic F108 | 5.0 | 9.0 |

EXAMPLE 9A
Tumor treatment

A multidrug-resistant tumor cell line was created by multiple passaging the murine myeloma SP2/0 cell line in the presence of 100 ng/ml of daunorubicin. The resistant cell line, SP2/0$^{dnr}$, was found to 10-fold more resistant to epirubicin ($IC_{50}$=0.7 µg/ml for the parent cell line; $IC_{50}$=8.0 µg/ml for SP2/0$^{dnr}$ line). When these resistant cells were used to form tumors in mice and, 50 days after the development of solid tumors, cells were recovered from the tumors, the recovered cells exhibited the same resistance.

Figure 7:
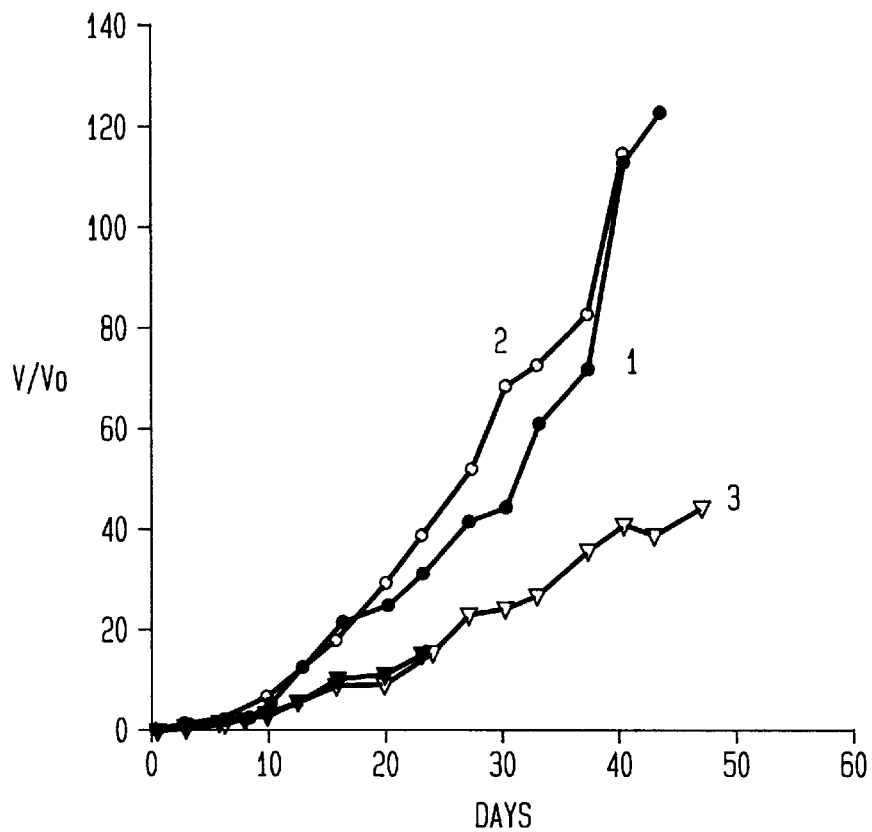
FIG. 7 shows the change, during a course of treatment, in the volume of multidrug-resistant Sp2/0$^{dnr}$ myeloma tumors in BALB/c mice. Volume was quantified as the mean tumor volume on a given day (V) over the mean volume on the first day of treatment (V$_0$).

The SP2/0$^{dnr}$ cells ($3 \times 10^6$ cells) were injected subcutaneously into 6-week old BALB/c mice. On treatment day 0, which occurred 14 days after the injection of tumor cells, the mice were treated by i.v. injection 20 μl/20 of body weight of (1) saline, (2) an isotonic solution of epirubicin (5 mg/kg body weight) or (3) an isotonic solution of epirubicin dissolved in 1% Pluronic P85 (1 mg/kg body weight). The results, expressed as the change of the ratio of the mean volume of the tumors (V) to the mean volume of the tumors on treatment day 0 ($V_0$) over a 60 day course of treatment, are shown in FIG. 7. Similar results were obtained with daunorubicin and with Pluronics L61 and F108.

EXAMPLE 9B

Optimal therapeutic dose

The same procedure as described in Example 9A was used, except that the parental cell line (SP2/0, a non-resistant cell line) cell line was used and the copolymer used and the concentrations used were as follows:

| copolymer | Concentrations (% w/v) | | |
|---|---|---|---|
| Pluronic F108 | 10% | 5% | 3% |
| Pluronic P85 | 10% | 1% | 0.5% |
| Pluronic L61 | 1% | 0.1% | 0.01% |

For Pluronic F108, the optimal antitumor efficacy was achieved using 10% copolymer. For Pluronic P85, the optimal antitumor efficacy was achieved using 1% copolymer. For Pluronic L61, the optimal antitumor efficacy was achieved using 0.1% copolymer. These values were designated the optimal therapeutic doses (OTDs) for the respective copolymers.

EXAMPLE 9C

Time course using OTD amounts of copolymer

Figure 8:
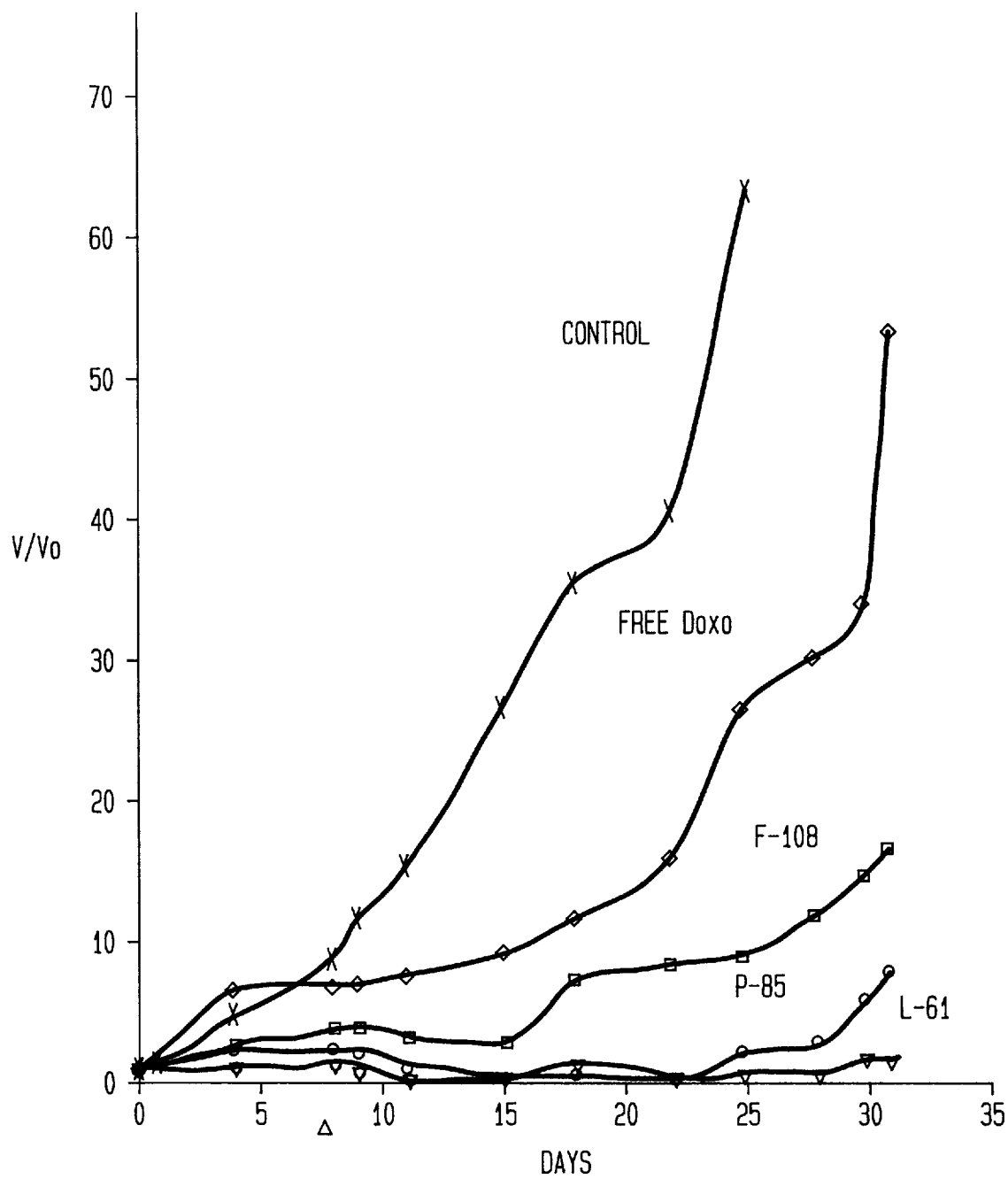
FIG. 8 shows the change, during a course of treatment, in the volume of multidrug-resistant Sp2/0$^{dnr}$ myeloma tumors in BALB/c mice.

The same procedure as in Example 9B was substituting the OTD amount of each of Pluronic F108, Pluronic P85 and Pluronic L61 as the vehicle for epirubicin. The results are shown in FIG. 8 (ordinate shows $V/V_0$).

EXAMPLE 10

Pluronic F68 was diluted with RPMI 1640 medium to a final concentration of 2.0% at 4° C. The mixture was incubated for 30 minutes at 37° C. and then sterilized by filtration through a 0.22 μm filter. An equal volume of a solution of 200 μg daunorubicin in RPMI 1640 medium added and this mixture was incubated for 30 minutes at 37° C.

Human ovarian carcinoma cells (CRL157 cells) were precultured in 1% solution of the Pluronic F68 in RPMI 1640 medium supplemented with 10% calf fetal serum. The daunorubicin/Pluronic solution was added and the mixture was incubated for 60 minutes at 37° C. and the cells then washed three times with RPMI 1640 and cultured in RPMI 1640 supplemented with 10% calf fetal serum for 3 days. Cytotoxicity was measured, both for this preparation and a parallel preparation of free daunorubicin, using the method of Alley et al., *Cancer Res.*, 48, 589–601 (1988). The results were as follows:

| conc. (ng/Ml) | 50000 | 10000 | 2000 | 400 | 80 | 16 |
|---|---|---|---|---|---|---|
| | | | % Inhibition | | | |
| Chemotherapeutic drug + Pluronic | 100 | 100 | 92 | 24 | 6 | 2 |
| Free drug | 100 | 81 | 53 | 38 | 20 | 1 |

Following the same procedure, cytotoxicity was determined against human T-lymphoma (Jurkat) cells:

| conc. (ng/ml) | 50000 | 10000 | 200 | 400 | 80 | 16 | 3.2 |
|---|---|---|---|---|---|---|---|
| | | | | % Inhibition | | | |
| Chemotherapeutic drug + Pluronic | 100 | 100 | 100 | 100 | 92 | 33 | 3 |
| Free drug | 100 | 100 | 100 | 84 | 51 | 44 | 22 |

Following the same procedure, cytotoxicity was determined against human small cell carcinoma of lung (H-69):

| conc. (ng/ml) | 50000 | 10000 | 200 | 400 | 80 | 16 | 3.2 |
|---|---|---|---|---|---|---|---|
| | | | | % Inhibition | | | |
| Chemotherapeutic drug + Pluronic | 100 | 100 | 100 | 100 | 100 | 42 | 12 |
| Free drug | 100 | 100 | 100 | 91 | 69 | 42 | 20 |

EXAMPLE 11

Block copolymers of poly(oxyethylene)-poly (oxypropylene) having the ratios of poly(oxypropylene) to poly(oxyethylene) indicated below were dispersed in RPMI 1640 medium at the concentrations indicated below. The mixtures were incubated for 40 minutes at 30° C. The average micelle diameter was measured by quasielastic light scattering. See Kabanov et al., *Macromolecules* 28: 2303–2314, 1995. The results were as follows:

| copolymer | conc. | Avg. Diameter |
|---|---|---|
| F-68 | 1.0% | 726.0 nm |
| P-85 | 1.0% | 18.0 nm |
| L-64 | 1.0% | 20.4 nm |
| 1:1.5 P-85:L-64 | 0.01% | 17.0 nm |
| 1:2.5 F-68:L-64 | 1.0% | 33.5 nm |

EXAMPLE 12

A 1:1.5 mixture of Pluronic P85 and Pluronic L64 having individual ratios (n) of (oxypropylene) to (oxyethylene) blocks of 1.00 and 1.50, respectively, and a combined value (N) of 1.30, was diluted with RPMI 1640 medium to a final concentration of 2.0% at 4° C. The mixture was incubated for 30 minutes at 37° C. and then sterilized by filtration through a 0.22 μm filter. An equal volume of a solution of 200 μg daunorubicin in RPMI 1640 medium was added and this mixture was incubated for 30 minutes at 37° C.

Cytotoxicity to human ovarian cancer cells (CRL157 cells) was measured, both for this preparation and a parallel preparation of free daunorubicin as described in Example 3A. The results were as follows:

| | % Inhibition | | | | | | |
|---|---|---|---|---|---|---|---|
| conc. (ng/mL) | 50000 | 10000 | 2000 | 400 | 80 | 16 | 3.2 |
| Chemotherapeutic drug + Pluronic | 100 | 100 | 100 | 100 | 94 | 53 | 8 |
| Free drug | 100 | 100 | 81 | 50 | 29 | 10 | 2 |

The daunorubicin compositions were evaluated for cytotoxicity in (i) human T-lymphoma (Jurkat) cells and (ii) normal human mononuclear cells. The results were as follows:

| Cell | % Inhibition | | | | | | |
|---|---|---|---|---|---|---|---|
| conc.(ng/mL) | 50000 | 10000 | 2000 | 460 | 80 | 16 | 3.2 |
| Jur.[1] | 100 | 100 | 100 | 100 | 100 | 74 | 28 |
| Jur.[2] | 100 | 100 | 100 | 83 | 59 | 36 | 21 |
| Norm.[1] | 100 | 100 | 91 | 60 | 21 | 5 | 2 |
| Norm.[2] | 100 | 100 | 80 | 58 | 23 | 18 | 1 |

[1]Treated with chemotherapetic drug + pluronic.
[2]Treated with free (non-micellar) chemotherapeutic drug.

EXAMPLE 13

$IC_{50}$ values for (i) human T-lymphoma (Jurkat) cells and (ii) normal human mononuclear cells were determined for the daunorubicin composition of Example 12 and compared to those for free daunorubicin. Measurements were made at the indicated intervals of the drug contact with the cells. The results were as follows:

| Cell | $IC_{50}$ (ng/mL) | | | | | | | |
|---|---|---|---|---|---|---|---|---|
| time (hours) | 0.25 | 0.50 | 0.75 | 1.0 | 2.0 | 4.0 | 8.0 | 12 |
| Jur.[1] | 150 | 46 | 25 | 17 | 9.0 | 0.80 | 0.50 | 0.30 |
| Jur.[2] | 120 | 68 | 35 | 25 | 19 | 16 | 3.0 | 5.2 |
| Norm[1] | 3570 | 950 | 620 | 450 | 250 | 220 | 160 | 140 |
| Norm[2] | 4900 | 980 | 405 | 310 | 290 | 275 | 280 | 240 |

[1]Treated with chemotherapetic drug + pluronic.
[2]Treated with free (non-micellar) chemotherapeutic drug.

EXAMPLE 14

The antineoplastic agent vinblastine was incorporated into the block copolymer mixture described in Example 12. The $IC_{50}$ of this preparation against SK cells was determined to be 0.121 µg/mL; the $IC_{50}$ against SK-resistant cells was 0.0012 µg/mL. The $IC_{50}$ values for free vinblastine were determined to be 0.095 µg/mL against SK cells and 0.615 µg/mL against SK-resistant cells.

EXAMPLE 15

The antineoplastic agent mitomycin C was incorporated into the block copolymer mixture described in Example 12. The $IC_{50}$ of this preparation against SK cells determined to be 0.265 µg/mL; the $IC_{50}$ against SK-resistant cells was 0.005 µg/mL. The $IC_{50}$ of free mitomycin C against SK cells was determined to be 0.320 µg/mL; the $IC_{50}$ against SK-resistant cells was 1.120 µg/mL.

EXAMPLE 16

The antineoplastic agent methotrexate was incorporated into the block copolymer mixture described in Example 12. The $IC_{50}$ of this preparation against SK cells was determined to be 0.880 µg/mL; the $IC_{50}$ against SK-resistant cells was 0.0175 µg/mL. The $IC_{50}$ of free methotrexate against SK cells was determined to be 1.090 µg/mL; and against SK-resistant cells was 1.340 µg/mL.

EXAMPLE 17

The antineoplastic agent colchicine was incorporated into the block copolymer mixture described in Example 12. The $IC_{50}$ of this preparation against SK cells was determined to be 0.720 µg/mL; the $IC_{50}$ against SK-resistant cells was 0.045 µg/mL. The $IC_{50}$ of free colchicine against SK cells was determined to be 0.950 µg/mL; and against SK-resistant cells was 7.450 µg/mL.

EXAMPLE 18

The antineoplastic agent daunorubicin was incorporated into the block copolymer mixture described in Example 12. The $IC_{50}$ of this preparation against SK cells was determined to be 0.600 µg/mL; the $IC_{50}$ against SK-resistant cells was 0.0068 µg/mL. The $IC_{50}$ of free daunorubicin against SK cells was determined to be 0.620 µg/mL; and against SK-resistant cells was 5.850 µg/mL.

EXAMPLE 19

To 30 µL of a 20 mg/mL solution of bovine serum albumin in phosphate buffered saline were added 30 µL of daunorubicin solution in the block copolymer mixture described in Example 12. A second formulation was prepared in parallel fashion using free daunorubicin.

The preparations were incubated for 10 minutes at 25° C., and then analyzed by HPLC on a TSK-3000 SW gel-filtration column in PBS containing 0.3M sodium chloride and 5% acetonitrile. Detection was performed at 280 nm and 470 nm. The portion of the drug bound with BSA determined as:

$$Db = Sb/Sf$$

in which:

Sb is the relative area of the 470 nm peak (corresponding to daunorubicin) which coincides in retention time for the 280 nm peak (corresponding to BSA); and Sf is the relative area of the peak (or peaks) corresponding to daunorubicin which does not coincide in retention time of the BSA peak.

The results were as follows:

| Composition | Db |
|---|---|
| Chemotherapeutic drug + Pluronic | 0.01 |
| Free drug | 0.39 |

EXAMPLE 20

Micellar daunorubicin obtained as described in Example 12 and free daunorubicin were incubated in the dark at 37° C. and cytotoxicity to CRL157 cells (human ovarian carcinoma cells) was then determined in the manner described in Example 1.

The results were as follows:

| time (hours): | 2 | 4 | 12 | 24 | 48 | 96 |
|---|---|---|---|---|---|---|
| | | | $IC_{50}$, µg/mL | | | |
| Chemotherapeutic + Pluronic | 9.1 | 10.05 | 9.8 | 10.4 | 10.7 | 11.3 |
| Free drug | 400 | 475 | 1120 | 6300 | 10180 | 48900 |

EXAMPLE 21

The daunorubicin composition of Example 12 and free daunorubicin were evaluated against daunorubicin-sensitive human breast cancer cells (MCF7 cells) and two drug resistant cell lines: daunorubicin/verapamil-resistant (MCF-7AU) not expressing P-170, and daunorubicin-resistant, verapamil-sensitive (MCF7-ADR®), expressing P-170. These cells were provided by the Cell Bank of the Moscow Research Center of Molecular Diagnostics, Moscow, Russia. The results were as follows:

| conc.(ng/mL) | 50000 | 10000 | 2000 | 400 | 80 | 16 |
|---|---|---|---|---|---|---|
| | | | % Inhibition | | | |
| MCF-7[1] | 100 | 100 | 84 | 65 | 42 | 12 |
| MCF-7AU[1] | 100 | 100 | 100 | 98 | 69 | 39 |
| MCF7-ADR[c1] | 100 | 100 | 100 | 89 | 73 | 45 |
| MCF-7[2] | 100 | 100 | 91 | 69 | 43 | 15 |
| MCF-7AU | 100 | 89 | 65 | 37 | 9 | 3 |
| MCF7-ADR[c2] | 100 | 86 | 62 | 39 | 7 | 2 |

[1]Treated with chemotherapeutic drug + pluronic.
[2]Treated with free (non-micellar) chemotherapeutic drug.

Free daunorubicin exhibits higher $IC_{50}$'s (is less toxic) against both resistant lines. Daunorubicin incorporated in the block copolymers exhibited lower $IC_{50}$'s (more toxic) against both resistant lines.

EXAMPLE 22

Groups (6 animals/dose point) of C57B1/6 7-week-old female mice were inoculated i.p. with free or micellar daunorubicin obtained as described in Example 12. The mice were observed for 14 days. Drug concentrations were adjusted so that a maximum volume of 0.5 mL was injected in each mouse.

The MTD was defined as the maximum dose which leads to no daunorubicin-deaths (any higher dose leads to the daunorubicin-related death of at least 1 animal per group). The experiment was repeated twice. The results were reproducible with less that 10% variation.

The MTD of free and micellar daunorubicin was determined to be 2.0 and 1.0 µg/kg body weight, respectively.

EXAMPLE 23

Daunorubicin causes bone marrow repression and leads to reversible leukopenia, i.e., a decrease in the number of white blood cells (leukocyte count) during drug administration. Bone marrow suppression, as well as anticancer effects of daunorubicin, are believed to be due to DNA-intercollating activity, whereas the most harmful side effect of anthracyclines, cardiotoxicity, are believed to result mainly from metabolites (which have low anticancer activity and do not produce significant effects on bone marrow). Therefore, the leukocyte count during in vivo administration of an MTD of daunorubicin allows for the assessment of the ratio between specific (DNA-intercalation) activity of the drug and non-specific toxicity.

Groups (6 animals/group) of C57B1/6 7-week-old female mice were inoculated i.p. with free or micellar daunorubicin obtained as described in Example 12. Drug formulations comprising the MTD for the respective formulation were adjusted so that a maximum volume of 0.5 mL was injected in each mouse. Blood samples were collected and viable leukocytes were counted as described in Michisch et al. *Proc. Natl. Acad. Sci.* USA 88, 547–551 (1991). The number of WBC after administration of 0.1 mL PBS was used as the control. This value was 15–16 million cells/ml. The experiment was repeated twice. The results were reproducible with less than 10% variation.

The results obtained were as follows:

| | WBS, % of control | | | | |
|---|---|---|---|---|---|
| Days | 0 | 3 | 7 | 10 | 14 |
| Chemotherapeutic + Pluronic | 100 | 20 | 46.6 | 86.6 | 100 |
| Free drug | 100 | 40 | 60 | 93.8 | 100 |

EXAMPLE 24

The effects of free and micellar daunorubicin obtained as described in Example 12 on leukocyte count were determined three days after administration as described in Example 23.

The results obtained were as follows:

| Dose of daunorubicin % of MTD | 25 | 50 | 75 | 100 |
|---|---|---|---|---|
| | WBS, % of control | | | |
| Chemotherapeutic drug + Pluronic | 85 | 73 | 45 | 21 |
| Free drug | 78 | 61 | 36 | 39 |

The data shown in Examples 22 through 24 indicate that solubilization of daunorubicin in the block copolymer micelles does not markedly affect the drug's overall toxicity (MTD of 2 mg/kg and 1 mg/kg for free and micellar drug, respectively), whereas solubilization increases bone marrow suppression indicating an increase in anticancer potency.

EXAMPLE 25

Anti-neoplastic activity was determined by evaluating the cytotoxic activity of plasma of mammals inoculated with the test compositions (see de Valeriola et al., *Cancer Chemother. Pharmacol.* 29, 133–140, 1991).

Groups (6 animals/group) of C57Bl/6 7-week-old female mice were inoculated i.v. (via the tail vein) with free or micellar daunorubicin obtained as described in Example 12. Drug formulations comprising the MTD for the respective formulation were adjusted so that a maximum volume of 0.1 mL was injected in each mouse. The experiment was repeated twice. The results were reproducible with less than 10% variation.

To obtain plasma samples, blood (10 μL) collected from the tail artery one hour after drug administration, diluted 1:10 with sterile RPMI 1640 medium, and centrifuged at 400 g for 15 minutes. The supernatants obtained were diluted as shown in the table with plasma analogously obtained from mice not inoculated with the drug (the plasma of mice not inoculated with the drug does not produce any significant cytotoxic effect on H-69 cells) and mixed with an equal volume of a suspension of H-69 cells in RPMI 1640 medium supplemented with 10% fetal calf serum. The cells were incubated for two hours at 37° C. and 5% C02, and then washed three times with RPMI 1640. The pretreated cells were incubated in RPMI 1640 supplemented with 10% fetal calf serum at 37° C. and 5% C02 for three days, after which cytotoxicity determined as described in Example 10.

The results obtained were as follows:

| Dilution of Plasma | 1:20 | 1:200 | 1:2000 | 1:20000 |
|---|---|---|---|---|
| | Inhibition, % | | | |
| Chemotherapeutic drug + Pluronic | 100 | 58 | 8 | 0 |
| Free drug | 42 | 5 | 0 | 0 |

Thus, the serum from mice treated with the micellar formulation had much greater cytotoxic potency.

EXAMPLE 26

The procedure of Example 25 was repeated utilizing SK cells and SK-resistant cells. The results were as follows:

a) When a dose equaling the MTD of a formulation of daunorubicin was introduced into the mice and the cytotoxicity of the resulting plasma measured, the results were:

| Plasma Dilution | 1:20 | 1:200 | 1:2000 |
|---|---|---|---|
| | Inhibition, % | | |
| SK-resistant[1] | 82 | 61 | 18 |
| SK-resistant[2] | 0 | 0 | 0 |
| SK[1] | 11 | 0 | 0 |
| SK[2] | 9 | 0 | 0 |

[1] Treated with chemotherapeutic drug + pluronic.
[2] Treated with free (non-micellar) chemotherapeutic drug.

b) When 10 mg/kg daunorubicin was introduced into each mouse the resulting plasma cytotoxicities were:

| Plasma Dilution | 1:20 | 1:200 | 1:2000 |
|---|---|---|---|
| | Inhibition, % | | |
| SK-resistant[1] | 100 | 94 | 69 |
| SK-resistant[2] | 8 | 0 | 0 |
| SK[1] | 62 | 31 | 0 |
| SK[2] | 22 | 6 | 0 |

[1] Treated with chemotherapeutic drug + pluronic.
[2] Treated with free (non-micellar) chemotherapeutic drug.

EXAMPLE 27

Fluconazole treatment of candida

Culture media

The medium used for susceptibility testing was high resolution (HR) medium. This medium is optimal for fluconazole testing and is prepared in two parts as follows. Part A comprises 0.2M phosphate buffer pH 7.5 made using $Na_2HPO_4$ sterilized by autoclaving. Part B comprises 2.93 g of HR powder (Unipath) and 0.2 g of sodium bicarbonate dissolved in 100 ml of deionized water, this is then sterilized by filtration and stored at 4° C. Prior to use, equal quantities of Part A and B are mixed.

Organisms

The organisms used in this study were fresh clinical isolates of Candida species or control organisms used for routine susceptibility testing of antifungal agents. The isolates were selected to cover a range of fluconazole sensitivities ranging from fluconazole sensitive (minimum inhibitory concentration (MIC) of 0.2 μg/ml) to fluconazole resistant (MIC of 100 μg/ml). All isolates were subcultered onto Sabourauds agar and incubated for 48 hrs. prior to susceptibility testing.

Preparation of yeast suspensions

Suspensions of the yeast were prepared by touching five individual colonies and suspending them in sterile water to yield a slightly cloudy suspension. This suspension was then diluted 1:100 in HR medium to yield a suspension containing $2 \times 10^4$ organism/ml.

Polymer/fluconazole complexes

Polymers were obtained from Serva Chemicals, Germany. Complexes of polymer with fluconazole were prepared. Prior to use, each solution was filtered through a 0.4 μm filter (Sartorius) to ensure sterility.

Preparation of fluconazole/polymer dilutions

Five polyether block copolymers were evaluated initially to test the efficacy of fluconazole in the presence of polymer and in the absence. Dilutions of fluconazole/polymer solutions were made with solutions containing the same copolymer. By such dilution, stock solutions containing 1250 μg/ml fluconazole were made. This stock solutions were further diluted in polymer to give a range of fluconazole concentrations from 1250–2.5 μg/ml. As a control, fluconazole was dissolved in water to give a range of concentrations from 1250–2.5 μg/ml.

Minimum Inhibitory Concentration (MIC) tests

For MIC testing 8 μl of each dilution of fluconazole in polymer or in water was added to the wells of a sterile microtitre plate. Two sets of controls were also established containing either 8 μl of water of 8 μl of fluconazole free polymer. The former served as a drug free control; the latter assessed any effect of the polymer on the yeast. HR medium was then added to each well to make the volume up to 100 μl. Finally, 100μ of each yeast suspension was added to the respective row of fluconazole dilutions. Each yeast suspension was inoculated onto blood agar and Sabourauds agar to ensure purity and as a check on inoculum size. Each yeast was therefore tested against fluconazole at final concentrations of 50 μl/ml–0.1 μg/ml in five different polymers or in water. The final polymer concentration in each well was 4% and the final yeast concentration was $1\times10^4$ organisms/ml. The plates were mixed gently and then incubated for 48 hrs. at 37° C. in a moist atmosphere. Plates were examined visually after 24 hrs. At 48 hrs., the plates were shaken on a rotary mixer for five minutes to suspend the yeast cells in the medium and then the OD490 was measured using sterile culture medium as a blank.

Interpretation of MIC

For each organism, growth was assessed in the drug free positive control well, this was then compared with the polymer control well, if the OD490 of the polymer containing well was <90% of the OD490 of the control well, then the polymer was assumed to have an intrinsic inhibitory effect on the organism and the MIC result was invalid. If the OD490 of the polymer control was >90% of the positive control, then no inhibitory effect was assumed to occur and the rest of the results were interpreted.

For each polymer and organism, the MIC was taken as the lowest fluconazole concentration which reduced growth (OD490) by ≧50% of the OD490 of the positive control. The following breakpoints were used for isolates in this study <6.2 μg/ml-Sensitive, 6.2 and 12.5 μg/ml—Intermediate sensitivity and >12.5 μg/ml—Resistant. The results were as follows:

| Organism | Species | Fluconazole | F68 + Flucon. | F108 + Flucon. | P85 + Flucon. |
|---|---|---|---|---|---|
| 1936 | C. albicans | >50 | 50 | 50 | 25 |
| 1904 | C. albicans | 50 | 50 | 50 | 25 |
| 1905 | C. kruzei | >50 | >50 | >50 | >50 |
| 1803 | C. albicans | 1.5 | 0.8 | 0.3 | 0.4 |
| 1961 | C. glabrata | 3.1 | 1.5 | 0.4 | 0.8 |
| Y01-09 | C. albicans | 0.4 | 0.2 | 0.1 | 0.2 |
| 2026 | C. albians | 6.2 | 6.2 | 0.8 | 1.5 |
| 1996 | C. glabrata | 6.2 | 3.1 | 1.5 | 1.5 |

Minimum inhibitory concentration (MIC), μg/ml

EXAMPLE 28

The activity of TNFα

The cytotoxic activity of TNFα with respect to resistant SK-cells was determined using the XTT assay as described in Example 3A. TNFα was added to cells for 24 hours at various concentrations: 1) free TNFα; b) TNFα in 0.1% Pluronic P85 and c) TNFα in 0.01% Pluronic L61. After 24 hour incubation with TNFα the cells were washed with RPMI-1640 and analyzed by XTT assay. All experimental points were triplicates. Data were mean ±SEM. The results were as follows:

| TNFα concentration (nM) | TNFα | +Pluronic P85 | +Pluronic L61 |
|---|---|---|---|
| 0.01 | 0 | 7 | 40 |
| 0.05 | 4 | 20 | 65 |
| 0.2 | 5 | 42 | 90 |
| 1.0 | 4 | 80 | 100 |
| 5 | 16 | 98 | 100 |
| 20 | 19 | 100 | 100 |
| 50 | 30 | 100 | 100 |
| 100 | 50 | 100 | 100 |
| 200 | 90 | 100 | 100 |

Cytotoxicity, %

EXAMPLE 29

Treatment of experimental glioma tumor.

The antibodies (Ab) to GFAP and α2-glycoprotein were modified with stearic acid residues as described in example 1. They were also covalently linked to Pluronic P85 as described by Kabanov et al. J. Controlled Release, 22:141 (1992).

The therapeutic efficacy of doxorubicin in treatment of glioma was explored. C6 glioma cells were inoculated intracerebrally in groups (n=25) of male Sprague-Dawley rats (280–300 g) obtained from Kriukovo Department of Nursery of Russian Academy of Sciences. 10, 15, 20, and 25 days after inoculation, (a) 10 mg/kg of free doxorubicin, (b) doxorubicin in 1% Pluronic P85, (c) doxorubicin in 10% Pluronic P85 containing 0.1 mg/ml of Ab modified with stearic acid chloride and (d) doxorubicin in 10% Pluronic P85 containing 0.1 mg/ml of Ab linked to Pluronic P85 were administered i.p. (volume 1 ml/300 g body weight). Controls will be given injections i.p. with an equal volume of saline. Clinical observations were performed daily. Animals were weighted weekly in the first 2 months and monthly thereafter. Vital signs will be verified to ensure that the animal was dead and necropsy was initiated within 5 min. after the animal died. Data on survival was analyzed to grade the drug effect on tumor incidence and latency. The data were presented as a ratio of median survival times in the treated group (T) and control (C). For necropsy all major organs were saved and fixed in their entirety. The tail (used in the study for animal identification during in-life phase) was saved in formalin with the animal tissues. All brains were removed and trimmed at three different positions. Three sections of the spinal cord were collected at the cervical, thoracic and lumbar level. Trimmed specimen was placed in Tissue Tek cassettes and processed in a tissue processor. Tissue sections were cut at a thickness of 4–6 mm using a microtome and stained with haematoxylin-eosine. Histopathological examinations of brains assessed: (i) the total number of tumors in animals; (ii) the number of tumor bearing animals; and (iii) the histopathological classification and grading of tumors. The results of the experiment are as follows:

| Animal group | Median survival, days | Trial/control x 100% |
|---|---|---|
| Control | 11.2 | — |
| Free doxorubicin | 10.5 | — |
| Micellar doxorubicin | 25.3 | 226 |
| Micellar doxorubicin + strearoytated antibodies | 41.0 | 366 |
| Micellar doxorubicin + conjugated antibodies | 24.5 | 218 |

The histopathological examinations also revealed that 1) free doxorubicin caused no effect on tumor size and number compared to control; 2) all 3 micellar formulations caused significant decrease in tumor size and number; 3) the most pronounced effect was observed in the case of micellar doxorubicin+strearoylated antibodies, in this case tumors were practically not observed.

EXAMPLE 30
Inhibition of Metastatic Processes

Figure 9:
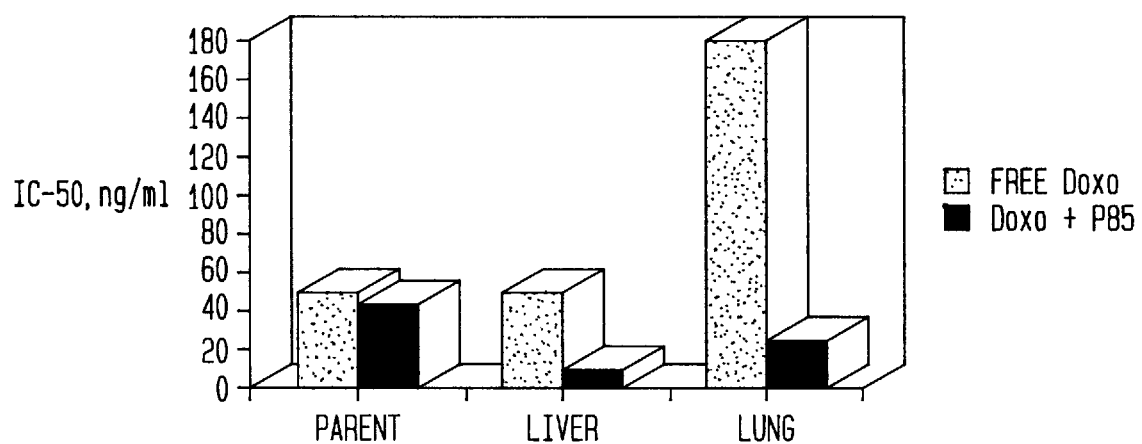
FIG. 9 shows the inhibition of tumor metastasis in mice treated with doxorubicin with Pluronic P85 vs. mice treated with doxorubicin alone.

Lewis lung carcinoma H59 cells ($2\times10^5$) were injected subcutaneously into 6-week old male C57B1/6 mice. Mice were sacrificed by $CO_2$ over-exposure on day 21 and the number and size of metastatic tumors was determined as described by Wilmanns, C; Fan, D.; O'Brian, C. A. et al. (1992) Int. J. Cancer Inst. 52, 98–104. The cancer cells injection resulted in formation of a solid tumor in the site of injection, and metastatic tumors in lung and liver. Tumor samples from 2 mice were harvested and adapted to culture as described by Dong, Z.; Radinsky, R.; Fan, D.; Tsan, R.; Bucana, C. D.; Wilmanns, C. and Fidler, I. J. (1994) Int. J. Cancer Inst. 86, 913–920. The in vitro sensitivity of the cell samples to free and micellar doxorubicin (in 0.01% Pluronic L61) was determined using XTT assay as described in Example 3A. The results are presented in FIG. 9. The metastatic cells in lung were characterized by resistance to free doxorubicin. This resistance was reversed in the case of micellar drug. The metastatic cells in liver were sensitive to free drug, their IC50 approximated the IC50 observed in parental H59 cell line. Still the cytotoxicity of the micellar drug with respect to liver metastatic cells was considerably higher than the cytotoxicity of the free drug.

EXAMPLE 31

A composition suitable for parental administration was prepared by dissolving 400 mg of Pluronic P-85 and 600 mg of Pluronic L-64 in 50 mL of RPMI 1640 at 4° C. The mixture was incubated for 30 minutes at 37° C. and then sterilized by filtration through a 0.22 μm filter. The filtered solution was mixed with a solution of 10 mg of sterile lyophilized daunorubicin powder dissolved in 50 mL of RPMI and incubated for 30 minutes at 37° C.

The composition can be stored in the dark at room temperature for 7 days without loss of activity or can be lyophilized and stored for at least 1 year in the dark at room temperature.

EXAMPLE 32

A further composition suitable for parenteral administration was prepared by dissolving 400 mg of Pluronic P-85 and 600 mg of Pluronic L-64 in 50 mL of PBS at 4° C. The mixture was incubated for 30 minutes at 37° C. and then was sterilized by filtration through a 0.22 μm filter. The filtered solution was mixed with a solution of 1 mg of sterile lyophilized daunorubicin powder and 5 mg of glucose dissolved in 50 mL of PBS and the mixture was incubated for 30 minutes at 37° C.

The composition can be stored in the dark at room temperature for 7 days without loss of activity or can be lyophilized and stored for at least 1 year in the dark at room temperature.

EXAMPLE 33

A further composition suitable for parenteral administration prepared by dissolving 100 mg of sodium ascorbate in 100 ml of a 9% aqueous solution of sodium chloride. To one-half of this solution were added at 4° C. 400 mg of Pluronic P-85 and 600 mg of Pluronic L-64. The mixture was incubated for 30 minutes at 37° C. and then sterilized by filtration through a 0.22 μm filter. Separately 10 mg of sterile lyophilized daunorubicin powder and 50 mg of glucose were dissolved in the remaining sodium ascorbate-sodium chloride solution and the two solutions were mixed and incubated for 30 minutes at 37° C.

This composition can be stored for 30 days in the dark at room temperature without loss of activity or can be lyophilized and stored for at least 1 year in the dark at room temperature.

EXAMPLE 34

A further composition suitable for parenteral administration is prepared by dissolving 100 mg of sodium ascorbate in 100 ml of a 9% aqueous solution of sodium chloride. To this solution are added at 4° C. 10 mg of Pluronic L-61. The mixture is incubated for 30 minutes at 37° C. and then sterilized by filtration through a 0.22 μm filter. This solution is packaged together with a container of 10 mg doxorubicin.

What is claimed:

1. A composition comprising:
   (a) an anticancer chemotherapeutic agent; and
   (b) a polyether block copolymer operable to form a fluid composition upon mixing with water, said block copolymer comprising a plurality of linear polymeric segments, the repeating units of which have molecular weights between about 30 and about 500, and wherein at least about 80% of the linkages joining the repeating units for each of the polymeric segments comprise an ether linkage, having a critical micellular concentration (CMC) of about 0.000001 to about 0.5%.

2. The composition of claim 1, wherein the composition: (i) comprises micelles comprising the polyether block copolymer, or (ii) forms micelles comprising the polyether block copolymer during the course of administration to an animal or subsequent thereto.

3. The composition of claim 2, wherein at least about 0.1% of the biological agent is in the micelles prior to or during the course of administration.

4. The composition of claim 3, wherein at least about 1% of the biological agent is in the micelles prior to or during the course of administration.

5. The composition of claim 1 wherein the polyether block copolymer comprises at least one polyether segment, said polyether segment comprising
   (a) a homopolymer of the ethyleneoxy monomer —$OCH_2CH_2$— or
   (b) a copolymer or block copolymer of said ethyleneoxy monomer and the monomer —$OCH(CH_3)CH_2$—,
and wherein each of said polyether segments having from about 5 to about 400 monomeric units.

6. The composition of claim 1 wherein the repeating units for each polymeric segment have molecular weight between about 30 and about 100.

7. The composition of claim 6 wherein at least about 90% of the linkages joining the repeating units for each polymeric segment comprise ether linkages.

8. The composition of claim 1 wherein each polymeric segment consists essentially of repeating units of formula —O—$R^5$, wherein $R^5$ is
   (1) —$(CH_2)_n$—$CH(R^6)$—, wherein n is zero or an integer from about 1 to about 5 and $R^6$ is hydrogen, cycloalkyl having about 3 to about 8 carbon atoms, alkyl having about 1 to about 6 carbon atoms, phenyl, alkylphenyl wherein the alkyl has about 1 to about 6 carbon atoms, hydroxy, hydroxyalkyl, wherein the alkyl has about 1 to about 6 carbon atoms, alkoxy having about 1 to about 6 carbon atoms, an alkyl carbonyl having about 2 to about 7 carbon atoms, alkoxycarbonyl, wherein the alkoxy has about 1 to about 6 carbon atoms, alkoxycarbonylalkyl, wherein the alkoxy and alkyl each independently has about 1 to about 6 carbon atoms, alkylcarboxyalkyl, wherein each alkyl independently has about 1 to about 6 carbon atoms, aminoalkyl wherein the alkyl has about 1 to about 6 carbon atoms, alkylamine or dialkylamino, wherein each alkyl independently has about 1 to about 6 carbon atoms, mono- or di-alkylaminoalkyl wherein each alkyl independently has about 1 to about 6 carbon atoms, chloro, chloroalkyl wherein the alkyl has from about 1 to about 6 carbon atoms, fluoro, fluoroalkyl wherein the alkyl has from about 1 to about 6 carbon atoms, cyano or cyano alkyl wherein the alkyl has from about 1 to about 6 carbon atoms or carboxyl;

(2) a carbocyclic group having about 3 to about 8 ring carbon atoms, wherein the group can be for example, cycloalkyl or aromatic groups, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substituents, or (3) a heterocyclic group, having about 3 to about 8 ring atoms, which can include heterocycloalkyl or heteroaromatic groups, which can include from about 1 to about 4 heteroatoms selected from the group consisting of oxygen, nitrogen, sulfur and mixtures thereto, and which can include alkyl having about 1 to about 6 carbons atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substituents.

9. The composition of claim 1, wherein the hydrophobe weight percentage of the polyether block copolymer is at least about 50%.

10. The composition of claim 9, wherein the hydrophobe weight percentage of the polyether block copolymer is at least about 60%.

11. The composition of claim 1, wherein the hydrophobe molecular weight of the polyether block copolymer is at least about 900.

12. The composition of claim 11, wherein the hydrophobe molecular weight of the polyether block copolymer is at least about 1700.

13. The composition of claim 12, wherein the hydrophobe molecular weight of the polyether block copolymer is at least about 2000 and the hydrophobe weight percentage is at least about 20%.

14. The composition of claim 13, wherein the hydrophobe molecular weight of the polyether block copolymer is at least about 2300 and the hydrophobe weight percentage is at least about 20%.

15. The composition of claim 1, wherein the polyether block copolymer has the formula:

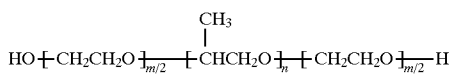

wherein n and m are integers of from about 4 to about 400.

16. The composition of claim 15, wherein the hydrophobe weight percentage of the polyether block copolymer is at least about 50%.

17. The composition of claim 16, wherein the hydrophobe weight percentage of the polyether block copolymer is at least about 60%.

18. The composition of claim 15, wherein the hydrophobe molecular weight of the polyether block copolymer is at least about 900.

19. The composition of claim 18, wherein the hydrophobe molecular weight of the polyether block copolymer is at least about 1700.

20. The composition of claim 15, wherein the hydrophobe molecular weight of the polyether block copolymer is at least about 2000 and the hydrophobe weight percentage is at least about 20%.

21. The composition of claim 20, wherein the hydrophobe molecular weight of the polyether block copolymer is at least about 2300 and the hydrophobe weight percentage is at least about 20%.

22. The composition of claim 15, wherein the hydrophobe molecular weight of the polyether block copolymer is between about 1500 and about 2000 and the hydrophobe weight percentage is between about 85% and about 95%.

23. The composition of claim 15, wherein the hydrophobe molecular weight of the polyether block copolymer is between about 3000 and about 3500 and the hydrophobe weight percentage is between about 15% and about 25%.

24. The composition of claim 15, wherein the hydrophobe molecular weight of the polyether block copolymer is between about 3500 and about 4000 and the hydrophobe weight percentage is between about 25% and about 35%.

25. The composition of claim 1, wherein the anticancer chemotherapeutic agent is a vinca alkaloid, mitomycin-type antibiotic, bleomycin-type antibiotic, antifolate, colchicine, demecoline, etoposide, taxane or anthracycline antibiotic.

26. The composition of claim 25, wherein the anticancer chemotherapeutic agent is doxorubicin, daunorubicin, carminomycin, epirubicin, idarubicin, mithoxanthrone, 4-demethoxy-daunomycin, 11-deoxydaunorubicin, 13-deoxydaunorubicin, adriamycin-14-benzoate, adriamycin-14-octanoate or adriamycin-14-naphthaleneacetate.

27. A composition comprising:
(a) a biological agent
(b) a polyether block copolymer operable to form a fluid composition upon mixing with water, said block copolymer comprising a plurality of linear polymeric segments, the repeating units of which have molecular weight contributions between about 30 and about 500, and wherein at least about 80% of the linkages joining the repeating units for each of the polymeric segments comprise an ether linkage, wherein:
(i) the polyether block copolymer has a hydrophobe weight percentage of at least about 50%;
(ii) the polyether block copolymer has a hydrophobe molecular weight of at least 900; or
(iii) the composition comprises one or more of said polyether block copolymers comprising the composition having a CMC of about 0.5% wt/vol or less at 37° C. in an isotonic aqueous solution.

28. The composition of claim 27 wherein the polyether block copolymer comprises at least one polyether segment, said polyether segment comprising
(a) a homopolymer of the ethyleneoxy monomer —OCH$_2$CH$_2$— or
(b) a copolymer or block copolymer of said ethyleneoxy monomer and the monomer —OCH(CH$_3$)CH$_2$—, and wherein each of said polyether segments has from about 5 to about 400 monomeric units.

29. The compositions of claim 28 wherein the repeating units for each polymeric segment have molecular weight between about 30 and about 100.

30. The compositions of claim 29 wherein at least about 90% of the linkages joining the repeating units for each polymeric segment comprise ether linkages.

31. The composition of claim 4 wherein each polymeric segment consists essentially of repeating units of formula —O—R⁵, wherein R⁵ is
  (1) —(CH₂)ₙ—CH(R⁶)—, wherein n is zero or an integer from about 1 to about 5 and R⁶ is hydrogen, cycloalkyl having about 3 to about 8 carbon atoms, alkyl having about 1 to about 6 carbon atoms, phenyl, alkylphenyl wherein the alkyl has about 1 to about 6 carbon atoms, hydroxy, hydroxyalkyl, wherein the alkyl has about 1 to about 6 carbon atoms, alkoxy having about 1 to about 6 carbon atoms, an alkyl carbonyl having about 2 to about 7 carbon atoms, alkoxycarbonyl, wherein the alkoxy has about 1 to about 6 carbon atoms, alkoxycarbonylalkyl, wherein the alkoxy and alkyl each independently has about 1 to about 6 carbon atoms, alkylcarboxyalkyl, wherein each alkyl independently has about 1 to about 6 carbon atoms, aminoalkyl wherein the alkyl has about 1 to about 6 carbon atoms, alkylamine or dialkylamino, wherein each alkyl independently has about 1 to about 6 carbon atoms, mono- or di-alkylaminoalkyl wherein each alkyl independently has about 1 to about 6 carbon atoms, chloro, chloroalkyl wherein the alkyl has from about 1 to about 6 carbon atoms, fluoro, fluoroalkyl wherein the alkyl has from about 1 to about 6 carbon atoms, cyano or cyano alkyl wherein the alkyl has from about 1 to about 6 carbon atoms or carboxyl;
  (2) a carbocyclic group having about 3 to about 8 ring carbon atoms, wherein the group can be for example, cycloalkyl or aromatic groups, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substituents, or
  (3) a heterocyclic group, having about 3 to about 8 ring atoms, which can include heterocycloalkyl or heteroaromatic groups, which can include from about 1 to about 4 heteroatoms selected from the group consisting of oxygen, nitrogen, sulfur and mixtures thereto, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substituents.

32. The composition of claim 27, wherein the hydrophobe weight percentage of the polyether block copolymer is at least about 60%.

33. The composition of claim 27, wherein the hydrophobe molecular weight of the polyether block copolymer is at least about 1700.

34. The composition of claim 27, wherein the hydrophobe molecular weight of the polyether block copolymer is at least about 2000 and the hydrophobe weight percentage is at least about 20%.

35. The composition of claim 34, wherein the hydrophobe molecular weight of the polyether block copolymer is at least about 2300 and the hydrophobe weight percentage is at least about 20%.

36. The composition of claim 27, wherein the polyether block copolymers comprising the composition have a CMC of about 0.05% wt/vol or less at 37° C. in an isotonic aqueous solution.

37. The composition of claim 27, wherein the polyether block copolymer has the formula:

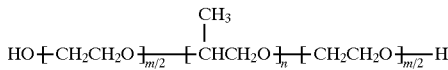

wherein n and m are integers between about 4 and about 400.

38. The composition of claim 37, wherein the hydrophobe weight percentage of the polyether block copolymer is at least about 60%.

39. The composition of claim 37, wherein the hydrophobe molecular weight of the polyether block copolymer is at least about 1700.

40. The composition of claim 38, wherein the hydrophobe molecular weight of the polyether block copolymer is at least about 2000 and the hydrophobe weight percentage is at least about 20%.

41. The composition of claim 40, wherein the hydrophobe molecular weight of the polyether block copolymer is at least about 2300 and the hydrophobe weight percentage is at least about 20%.

42. The composition of claim 27, wherein the biological agent is an amphotericin B, flucytosine, triazole, imidazole, β-lactam antibiotic, cephalosporins, tetracycline, beta-lactamase inhibitors, aminoglycosides, chloramphenicol, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides, trimethoprim-sulfamethoxazole, quinolones, methenamine, nitrofurantoin or phenazopyridine.

* * * * *

UNITED STATES PATENT AND TRADEMARK OFFICE
CERTIFICATE OF CORRECTION

PATENT NO. : 5,817,321
DATED : October 6, 1998
INVENTOR(S) : Alakhov, et al.

It is certified that error appears in the above-identified patent and that said Letters Patent is hereby corrected as shown below: On the title page, In the Inventors, item [75], should read "Valery Yu. Alakhov, Baie d'Urfe, Quebec, Canada; Alexander V. Kabanov, Omaha, Nebraska, USA; Peter G. Sveshnikov; Eugenii S. Severin, both of Moscow, Russian Federation Signed and Sealed this Eighteenth Day of May, 1999

Attest:

Q. TODD DICKINSON

*Attesting Officer*  Acting Commissioner of Patents and Trademarks

UNITED STATES PATENT AND TRADEMARK OFFICE
CERTIFICATE OF CORRECTION

PATENT NO. : 5,817,321
DATED : October 6, 1998
INVENTOR(S) : Alakhov, et al.

It is certified that error appears in the above-identified patent and that said Letters Patent is hereby corrected as shown below:

Claim 31,
Should read, "The composition of claim 30..."

REMARKS:
Claim 31 was originally numbered as claim 41. This original claim 41 depended on original claim 40, which depended on original claim 39, which depended on original claim 38. Applicants deleted original claims 39 and 40 in their Amendment and Response submitted on May 19, 1997. In the printed patent, original claim 38 was renumbered claim 30.

Signed and Sealed this

Fourth Day of September, 2001

*Attest:*

NICHOLAS P. GODICI
*Attesting Officer*     *Acting Director of the United States Patent and Trademark Office*